United States Patent
Furudono et al.

(10) Patent No.: US 11,026,453 B2
(45) Date of Patent: Jun. 8, 2021

(54) FLAVOR ASPIRATOR

(71) Applicant: JAPAN TOBACCO INC., Tokyo (JP)

(72) Inventors: Yuichi Furudono, Tokyo (JP); Kazuya Ishibashi, Tokyo (JP); Takuya Shiraishi, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 335 days.

(21) Appl. No.: 16/157,691

(22) Filed: Oct. 11, 2018

(65) Prior Publication Data

US 2019/0037929 A1    Feb. 7, 2019

Related U.S. Application Data

(63) Continuation of application No. PCT/JP2017/014778, filed on Apr. 11, 2017.

(30) Foreign Application Priority Data

Apr. 12, 2016 (JP) .............................. JP2016-079731

(51) Int. Cl.
*A24F 47/00* (2020.01)
*A24F 7/00* (2006.01)
*A61M 15/06* (2006.01)

(52) U.S. Cl.
CPC .............. *A24F 47/008* (2013.01); *A24F 7/00* (2013.01); *A24F 47/00* (2013.01); *A61M 15/06* (2013.01)

(58) Field of Classification Search
CPC .......... A24F 47/008; A24F 7/00; A24F 47/00; A61M 15/06
USPC ....................................................... 131/329
See application file for complete search history.

(56) References Cited

U.S. PATENT DOCUMENTS

| | | | |
|---|---|---|---|
| 4,687,006 A * | 8/1987 | Shelton | A24F 13/16 131/257 |
| 5,898,427 A | 4/1999 | Okamoto | |
| 9,004,073 B2 | 4/2015 | Tucker et al. | |
| 2006/0013642 A1 | 1/2006 | Kobayashi et al. | |
| 2013/0284190 A1 | 10/2013 | Scatterday et al. | |

(Continued)

FOREIGN PATENT DOCUMENTS

| | | |
|---|---|---|
| CA | 2925645 A1 | 4/2015 |
| CN | 1787922 A | 6/2006 |

(Continued)

OTHER PUBLICATIONS

Taiwanese Office Action and Search Report, dated Dec. 20, 2018, for Taiwanese Application No. 106112182, with an English translation.

(Continued)

*Primary Examiner* — Francisco W Tschen
*Assistant Examiner* — Guy F Mongelli
(74) *Attorney, Agent, or Firm* — Birch, Stewart, Kolasch & Birch, LLP

(57) ABSTRACT

A flavor aspirator includes: a weight-concentrated part that is provided at a position off the mouthpiece end and closer to the mouthpiece end side than to a midpoint position between the mouthpiece end and the distal end, and that accounts for at least approximately half of a total weight of the flavor aspirator. A value of (a length from the mouthpiece end to the center of gravity)/(a total length defined by a length from the mouthpiece end to the distal end) is in a range of 0.20 to 0.45.

18 Claims, 15 Drawing Sheets

| | Total length (mm) | Total weight (g) | (Length from mouthpiece end to center of gravity) /(total length) | Moment (gf·cm) | (Weight of first weight-concentrated part) /(total weight) (%) | (Weight of second weight-concentrated part) /(total weight) (%) |
|---|---|---|---|---|---|---|
| Conventional product 1 | 120 | 16.5 | 0.52 | 53.5 | 16 | 30 |
| Example A-1 | 100 | 13.9 | 0.22 | −11.8 | 46 | — |
| Example A-2 | 98 | 13.1 | 0.25 | −6.4 | 55 | — |
| Example A-3 | 100 | 13.9 | 0.30 | 0.0 | 72 | — |
| Example A-4 | 100 | 13.9 | 0.35 | 6.2 | 82 | — |
| Example A-5 | 100 | 10.4 | 0.44 | 14.5 | 50 | — |
| Example A-6 | 100 | 15.5 | 0.42 | 18.6 | 50 | — |
| Comparative example A-7 | 100 | 15.5 | 0.52 | 34.1 | 20 | — |
| Comparative example B-1 | 93 | 17.0 | 0.17 | −20.2 | — | 83 |
| Example B-2 | 95 | 11.9 | 0.21 | −10.1 | — | 85 |
| Example B-3 | 100 | 11.3 | 0.25 | −6.2 | — | 82 |
| Example B-4 | 100 | 13.5 | 0.30 | −0.7 | — | 86 |
| Example B-5 | 100 | 10.5 | 0.35 | 5.2 | — | 80 |
| Example B-6 | 100 | 10.5 | 0.41 | 11.6 | — | 50 |
| Example B-7 | 100 | 15.5 | 0.40 | 15.5 | — | 50 |
| Comparative example B-8 | 100 | 15.5 | 0.50 | 31.0 | — | 53 |

(56) References Cited

U.S. PATENT DOCUMENTS

| | | | |
|---|---|---|---|
| 2014/0196735 A1 | 7/2014 | Liu | |
| 2014/0246032 A1 | 9/2014 | Scatterday | |
| 2015/0122276 A1* | 5/2015 | Johnson | G08B 6/00 |
| | | | 131/329 |
| 2015/0122277 A1* | 5/2015 | Frobisher | A24D 3/041 |
| | | | 131/329 |
| 2016/0206004 A1 | 7/2016 | Shinkawa et al. | |
| 2016/0345625 A1 | 12/2016 | Liu | |

FOREIGN PATENT DOCUMENTS

| | | |
|---|---|---|
| CN | 204579896 U | 8/2015 |
| CN | 105636465 A | 6/2016 |
| JP | 57-4800 A | 1/1982 |
| JP | 7-306744 A | 11/1995 |
| JP | 9-38115 A | 2/1997 |
| JP | 2004-338235 A | 12/2004 |
| JP | 2012-166504 A | 9/2012 |
| WO | WO 2013/137084 A1 | 9/2013 |
| WO | WO 2015/046385 A1 | 4/2015 |
| WO | WO 2015/120586 A1 | 8/2015 |
| WO | WO 2015/120636 A1 | 8/2015 |

OTHER PUBLICATIONS

International Preliminary Report on Patentability and English translation of the Written Opinion of the International Searching Authority (Forms PCT/IB/326, PCT/IB/373, and PCT/ISA/237) for International Application No. PCT/JP2017/014778, dated Oct. 25, 2018.
International Search Report issued in PCT/JP2017/014778 (PCT/ISA/210), dated Jul. 4, 2017.
Written Opinion of the International Searching Authority issued in PCT/JP2017/014778 (PCT/ISA/237), dated Jul. 4, 2017.
Chinese Office Action and Search Report, dated Jul. 3, 2020, for Chinese Application No. 201780023463.1, with an English translation.
Extended European Search Report dated Dec. 4, 2019, for European Application No. 17782378.8.

* cited by examiner

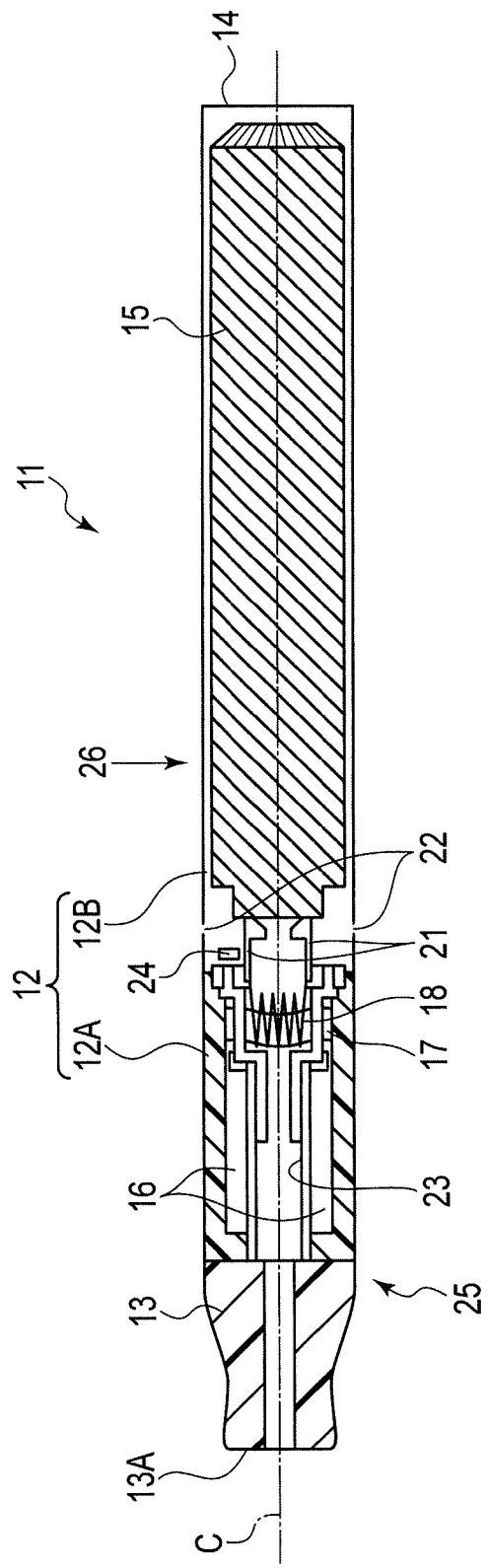
F I G. 2

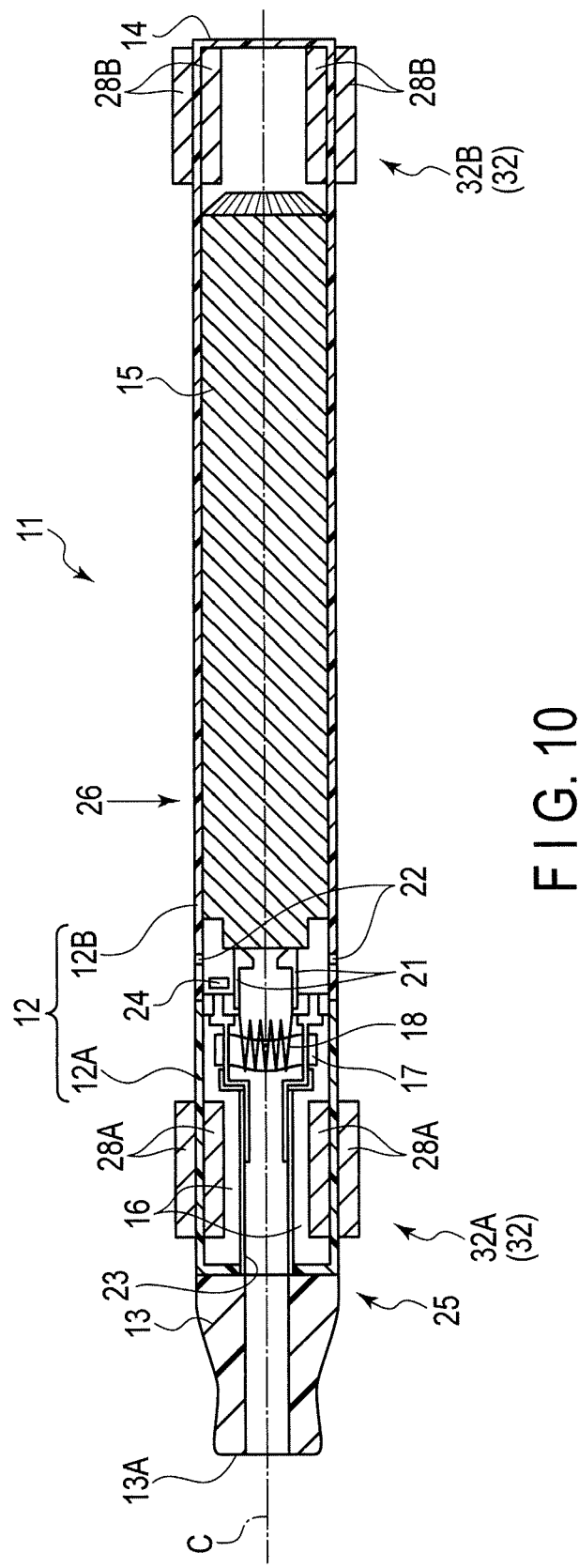
F I G. 10

| | Total length (mm) | Total weight (g) | (Length from mouthpiece end to center of gravity) /(total length) | Moment (gf·cm) | (Weight of first weight-concentrated part) /(total weight) (%) | (Weight of second weight-concentrated part) /(total weight) (%) |
|---|---|---|---|---|---|---|
| Conventional product 1 | 120 | 16.5 | 0.52 | 53.5 | 16 | 30 |
| Example A-1 | 100 | 13.9 | 0.22 | -11.8 | 46 | — |
| Example A-2 | 98 | 13.1 | 0.25 | -6.4 | 55 | — |
| Example A-3 | 100 | 13.9 | 0.30 | 0.0 | 72 | — |
| Example A-4 | 100 | 13.9 | 0.35 | 6.2 | 82 | — |
| Example A-5 | 100 | 10.4 | 0.44 | 14.5 | 50 | — |
| Example A-6 | 100 | 15.5 | 0.42 | 18.6 | 50 | — |
| Comparative example A-7 | 100 | 15.5 | 0.52 | 34.1 | 20 | — |
| Comparative example B-1 | 93 | 17.0 | 0.17 | -20.2 | — | 83 |
| Example B-2 | 95 | 11.9 | 0.21 | -10.1 | — | 85 |
| Example B-3 | 100 | 11.3 | 0.25 | -6.2 | — | 82 |
| Example B-4 | 100 | 13.5 | 0.30 | -0.7 | — | 86 |
| Example B-5 | 100 | 10.5 | 0.35 | 5.2 | — | 80 |
| Example B-6 | 100 | 10.5 | 0.41 | 11.6 | — | 50 |
| Example B-7 | 100 | 15.5 | 0.40 | 15.5 | — | 50 |
| Comparative example B-8 | 100 | 15.5 | 0.50 | 31.0 | — | 53 |

F I G. 12

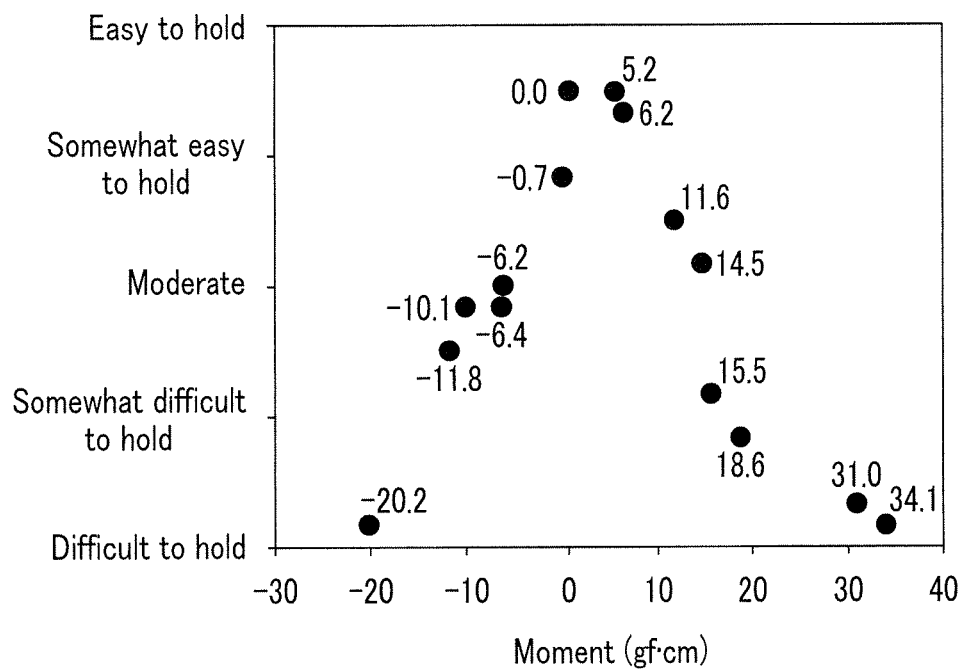
F I G. 16
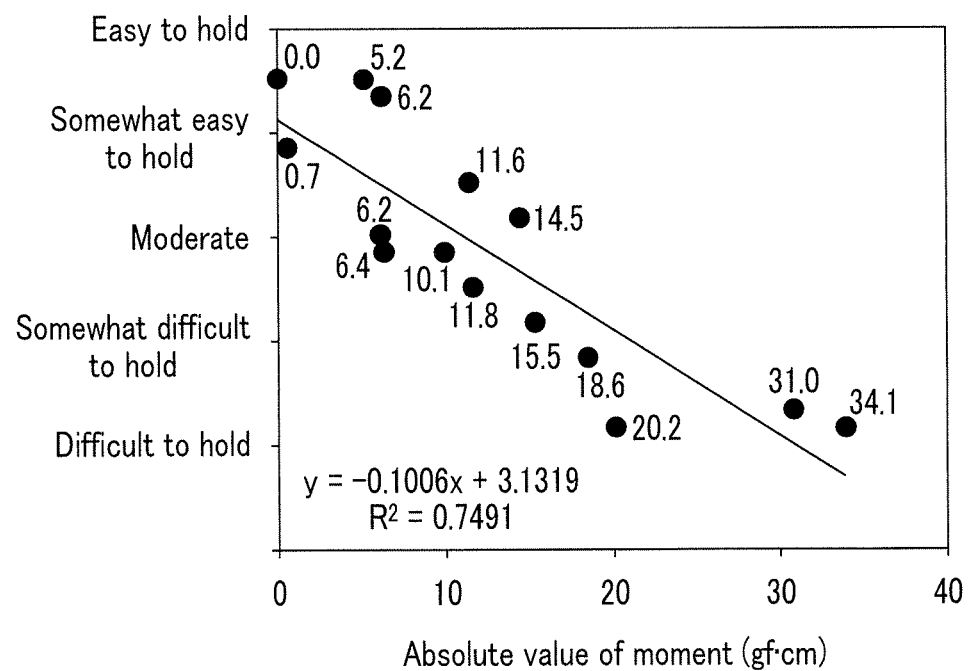
F I G. 17

FLAVOR ASPIRATOR

CROSS-REFERENCE TO RELATED APPLICATIONS

This application is a Continuation Application of PCT Application No. PCT/JP2017/014778, filed Apr. 11, 2017 and based upon and claiming the benefit of priority from prior Japanese Patent Application No. 2016-079731, filed Apr. 12, 2016, the entire contents of all of which are incorporated herein by reference.

FIELD

The present invention relates to a flavor aspirator that allows a user to inhale flavors from the end of its mouthpiece.

BACKGROUND

In Patent Literatures 1-3 listed below for example, paper is used for an outer cover of a flavor aspirator to imitate the touch and appearance of cigarettes. Patent Documents 4 and 5 listed below disclose an internal structure of the flavor aspirator.

CITATION LIST

Patent Literature

[Patent Document 1] US Patent Application Publication No. 2013/0284190

[Patent Document 2] US Patent Application Publication No. 2014/0246032

[Patent Document 3] US Patent Application Publication No. 2014/0196735

[Patent Document 4] International Publication No. 2015/120636

[Patent Document 5] International Publication No. 2015/120586

SUMMARY OF THE INVENTION

Technical Problem

A typical flavor aspirator is heavier than a cigarette. For this reason, when a user uses a flavor aspirator, a heavy load is applied to the user's fingers. A user has to increase the gripping force in order to properly hold the flavor aspirator, which makes the flavor aspirator difficult for a user to use. Furthermore, there have been problems that a user has to hold such a flavor aspirator with poor balance and no stability, and cannot easily put the flavor aspirator to the user's mouth to smoke.

An object of the present invention is to provide a flavor aspirator that enables a user to hold it with good balance and stability and so that it may be smoked easily.

Solution to Problem

A flavor aspirator extending from a mouthpiece end to a distal end in a form of a rod or a cylinder, the flavor aspirator includes: a weight-concentrated part that is provided at a position off the mouthpiece end and closer to the mouthpiece end side than to a midpoint position between the mouthpiece end and the distal end, and that accounts for at least approximately half of a total weight of the flavor aspirator, or that is provided in a part in a vicinity of the mouthpiece end and in a part in a vicinity of the distal end, and that has a weight accounting for at least approximately half of the total weight, the weight being a sum of the weight of the part in the vicinity of the mouthpiece end and the weight of the part in the vicinity of the distal end; and wherein a value of (a length from the mouthpiece end to the center of gravity)/(a total length defined by a length from the mouthpiece end to the distal end) is in a range of 0.20 to 0.45.

Advantageous Effects of Invention

According to the present invention, a flavor aspirator that enables a user to hold it with good balance and stability, and to be smoked easily, can be provided.

BRIEF DESCRIPTION OF THE DRAWINGS

FIG. 2 is a cross-sectional view of a flavor aspirator of a second embodiment, taken along a plane including a central axis.

FIG. 10 is a cross-sectional view of a flavor aspirator of a 10th embodiment, taken along a plane including a central axis.

FIG. 12 is a table showing conditions of examples, comparative examples, and a conventional product of flavor aspirators.

FIG. 16 is a graph showing a relationship between each of the results of the sensory evaluations shown in FIG. 15 and a rotation moment.

FIG. 17 is a graph showing a relationship between each of the results of the sensory evaluations shown in FIG. 15 and an absolute value of a rotation moment.

DETAILED DESCRIPTION

A flavor aspirator of the present invention is realized as, for example, a heating-type (non-combustion type) flavor aspirator that generates aerosol by heating a liquid supplied from an aerosol source, and that allows a user to inhale flavors, such as a tobacco flavor through the aerosol. Furthermore, a flavor aspirator can also be realized as a non-heating type flavor aspirator that generates aerosol or vapor without heating a liquid supplied from an aerosol source, and that allows a user to inhale flavors, such as a tobacco flavor, through the aerosol. The flavor aspirator can also be realized as a heating-type/non-heating type flavor aspirator that does not include tobacco flavors in its aerosol source and that allows a user to inhale non-tobacco flavors, such as mint or menthol.

First Embodiment

A first embodiment of the flavor aspirator will be described below with reference to the drawings. The first to eleventh embodiments to be described below are embodiments of a flavor aspirator 11 having an aerosol source, a heat source that heats a liquid supplied from the aerosol source and generates an aerosol, and a power supply that supplies power to the heat source. A total weight of the flavor aspirator 11, a weight of each constituent element, a position of the center of gravity, and a moment (rotation moment), which are referred to hereinafter, are those measured and calculated before the flavor aspirator 11 is used. This pre-use state refers to a state where the flavor aspirator 11 is ready to be used with a cover (if indeed there is one), being removed, the aerosol source has not been used even once, and the inside of the aerosol resource is filled up with a liquid.

Figure 1:
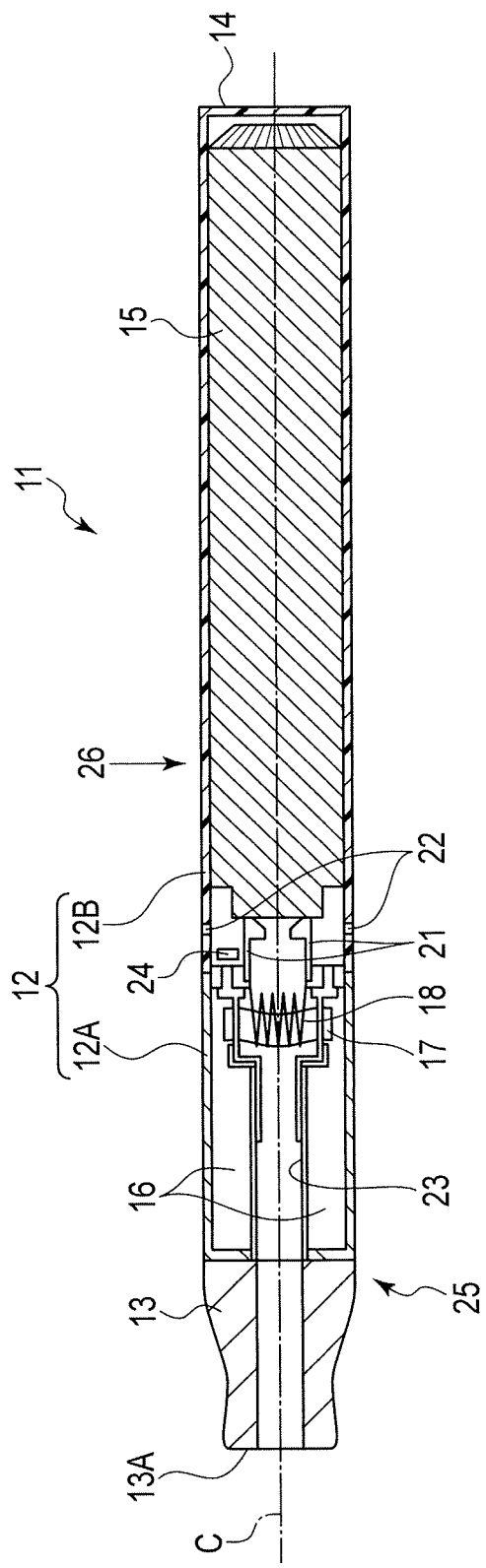
FIG. 1 is a cross-sectional view of a flavor aspirator of a first embodiment, taken along a plane including a central axis.

As shown in FIG. 1, the flavor aspirator 11 has a rod-like or columnar shape, extending from its mouthpiece end 13A to its distal end 14. The flavor aspirator 11 includes a cylindrical housing 12 constituting an outer shell, a cylindrical mouthpiece 13, a distal end 14 provided on the opposite side of the mouthpiece end 13A of the mouthpiece 13, a battery 15 housed in the housing 12, an aerosol source 16 housed in the housing 12, a wick 17 connected to the aerosol source 16, a heater 18 made of an electrically resistive metallic material wound around the wick 17, wiring 21 connecting the heater 18 to the battery 15, air-intake holes 22 provided in the housing 12, a ventilation path 23 provided in a cylindrical shape at the center of the housing 12, and a drive circuit 24 for controlling the supply of electric power to the heater 18. The total length, to be referred to hereinafter, is defined by the length from the mouthpiece end 13A to the distal end 14 of the flavor aspirator 11. The central axis C is an axis extending from the mouthpiece end 13A to the distal end 14 of the flavor aspirator 11. The wick 17 is formed by making a plurality of glass fibers (fibers) into one bundle, and the wick 17 is capable of supplying (sucking up) a liquid in the aerosol source 16 to the position of the heater 18 using the capillary force acting among the glass fibers.

The mouthpiece 13 is made of a metallic material such as stainless steel, brass, or the like. The housing 12 is formed in a cylindrical shape with, for example, a resin material. The housing 12 has a first part 12A positioned the mouthpiece end 13A side, and a second part 12B positioned on the distal end 14 side. The first part 12A is made of a metallic material similar to the material of the mouthpiece 13. The second part 12B is made of a resin material having a low specific gravity. As this resin material, for example, polycarbonate, polyacetal, polypropylene, fluororesin (Teflon (registered trademark)), or the like can be used. The battery 15 constitutes a power supply of the flavor aspirator 11. A cylindrical lithium battery is adopted as the battery 15, for example, but other batteries may be used. The battery 15 may be a rechargeable battery that can be repeatedly used.

The aerosol source 16 is composed of an absorbent, such as absorbent cotton, or other porous body impregnated with a liquid such as propylene glycol or glycerin containing a tobacco flavor and other flavors such as menthol. The aerosol source 16 may be composed of a sealable small solution tank in which propylene glycol, or glycerin containing a tobacco flavor and other flavors such as menthol, is enclosed. The aerosol source 16 does not necessarily include a tobacco flavor, and may enclose only a menthol flavor. At least one air-intake hole 22 is formed at a constant interval along the circumferential direction of the housing 12. In the present embodiment, a plurality of air-intake holes 22 are formed, but one air-intake hole 22 will suffice. Each air-intake hole 22 is constituted by a circular small hole penetrating the housing 12. The heater 18 constitutes a heat source for generating aerosol by heating a liquid supplied from the aerosol source 16.

In the present embodiment, the mouthpiece 13 and the first part 12A, both formed of a metallic material, constitute a first weight-concentrated part 25. The first weight-concentrated part 25 is provided at a position off the mouthpiece end 13A, and closer to the mouthpiece end 13A than to a midpoint position 26 between the mouthpiece end 13A and the distal end 14. More specifically, the first weight-concentrated part 25 is provided at a position where a value of (the length from the mouthpiece end 13A to the position)/(the total length) falls within the range of 0.15 to 0.45. The first weight-concentrated part 25 accounts for at least approximately half of the total weight of the flavor aspirator 11. More specifically, the first weight-concentrated part 25 has a value of (the length from the mouthpiece end 13A to the position)/(the total length) within the range of 0.15 to 0.45, and accounts for 45% or more of the total weight. More preferably, the first weight-concentrated part 25 has a value of (the length from the mouthpiece end 13A to the position)/(the total length) within the range of 0.15 to 0.45, and accounts for 50% or more and no more than 82% of the total weight.

The total weight of the flavor aspirator 11 is set as appropriate within the range of 10.0 g to 20.0 g. Preferably, the total weight of the flavor aspirator 11 lies in the range of 10.4 g to 15.5 g. Even more preferably, the total weight of the flavor aspirator 11 lies in the range of 10.4 g to 13.9 g. Note that the first weight-concentrated part 25 herein is realized by being heavier than the other parts of the flavor aspirator 11. Thus, the presence of the first weight-concentrated part 25 does not negate the arranging of a component having a large weight in a part other than the first weight-concentrated part 25.

In the present embodiment, a moment (rotation moment) in a case where a point with the value of 0.3 (the length from the mouthpiece end 13A to the point)/(the total length) is being gripped by hand (fingers) is set as follows: in this case, the absolute value of the moment is set to be, for example, 20.0 gf·cm or less. Preferably, the absolute value of the moment is set to be 15.5 gf·cm or less. On the other hand, the absolute value of the moment can also be set to 11.25 gf·cm or less as described later.

This moment M can be calculated by the following equation:

$$M = \text{(the total weight of the flavor aspirator 11)} \times \{\text{(the length from the mouthpiece end 13A to the center of gravity)} - \text{(the length from the mouthpiece end 13A to a gripping point)}\}$$

The center of gravity of the flavor aspirator 11 is set in such a manner that a value of (the length from the mouthpiece end 13A to the center of gravity)/(the total length) falls within the range of 0.20 to 0.45. Preferably, the position of the center of gravity is set in such a manner that a value of (the length from the mouthpiece end 13A to the center of gravity)/(the total length) falls within the range of 0.25 to 0.44. More preferably, the position of the center of gravity is set in such a manner that a value of (the length from the mouthpiece end 13A to the center of gravity)/(the total length) falls within the range of 0.3 to 0.44.

The operation of the flavor aspirator 11 is described herein. The flavor aspirator 11 is activated by pushing a switch such as a push button or the like provided in the housing 12, or by sensing a user's inhalation of the air through the mouthpiece 13 using a flow sensor. Alternatively, if the battery 15 is a rechargeable-type battery, the flavor aspirator 11 may be activated when removal of the battery 15 from the charger is sensed by a sensing unit provided in the flavor suction device 11.

When the flavor aspirator 11 is activated, the drive circuit 24 supplies electric power to the heater 18. Any method can be adopted to supply electric power; for example, electric power may be intermittently supplied to the heater 18 at a fixed time interval, or a certain voltage may be applied to the heater 18 after the flavor aspirator 11 is activated. Alternatively, a flow meter may be provided in the ventilation path 23, so that the electric power is increased or decreased in proportion to the flow rate of the gas passing through the ventilation path 23. The liquid supplied from the aerosol source 16 is heated by the heater 18 and mixed with the air supplied from the air-intake hole 22 to generate aerosol.

When the user inhales from the mouthpiece 13, the air is taken into the housing 12 from the air-intake holes 22. This air becomes aerosol containing a flavor (at least one of a tobacco flavor or a flavor such as menthol) when passing through the wick 17. This aerosol is taken into the oral cavity of the user, meaning the user is able to enjoy the flavor (incense flavor).

At this time, the user often grips a point between the midpoint position 26 and the mouthpiece end 13A with fingers. The inventors conducted surveys of users and found that users customarily tend to grip that particular point.

In the present embodiment, the first weight-concentrated part 25 is located in the vicinity of the gripping point, and the center of gravity of the flavor aspirator 11 is also located in the vicinity of the gripping point. For this reason, when the flavor aspirator 11 is substantially gripped horizontally with fingers, for example, it is possible to control the generation of an acting moment to the extent that the installation angle of the flavor aspirator 11 is changed.

According to the present embodiment, the flavor aspirator 11 extends from the mouthpiece end 13A to the distal end 14 in a rod-like or columnar shape, and has a weight-concentrated part that is provided at a position off the mouthpiece end 13A and closer to the mouthpiece end 13A side than to the midpoint position 26 between the mouthpiece end 13A and the distal end 14, and that accounts for at least approximately half of the total weight, and has a value of (the length from the mouthpiece end 13A to the center of gravity)/(the total length) in the range of 0.20 to 0.45. More specifically, the weight-concentrated part is positioned in such a manner that a value of (the length from the mouthpiece end 13A)/(the total length) is in the range of 0.15 to 0.45 and its weight accounts for 45% or more of the total weight. Even more preferably, the weight-concentrated part is positioned in such a manner that a value of (the length from the mouthpiece end 13A to the part)/(the total length) is in the range of 0.15 to 0.45 and its weight accounts for 50% or more and no more than 82% of the total weight.

As a result of having conducted user surveys, the inventors found that the users in the act of smoking, grip the vicinity of the position where the value of (the length from the mouthpiece end 13A to the position)/(the total length) is 0.3. According to the above-described design, the weight-concentrated part is positioned in the vicinity of the part gripped by the user, and the center of gravity of the flavor aspirator 11 is also located in the vicinity of the part gripped by the user. Thus, it is possible to control generation of an acting moment to the extent that the installation angle of the flavor aspirator 11 is changed, thereby achieving the conditions whereby the flavor aspirator 11 can be easily held. Furthermore, it is possible to reduce unnecessary force applied to the user's fingers to maintain the position of the flavor aspirator 11, thereby achieving the flavor aspirator 11 that causes less fatigue to the user.

Preferably, the absolute value of the moment when the point where a value of (the length from mouthpiece end to the point)/(the total length) of 0.3 is gripped is 15.5 gf·cm or less. This numerical range corresponds to Examples A-1 to A-5, which are described later. According to this design, it is possible to reduce an acting moment to the extent that the installation angle of the flavor aspirator 11 is changed when the flavor aspirator 11 is gripped, thereby achieving the flavor aspirator 11 that is easy for the user to hold and causes less fatigue to the user.

In the case where the absolute value of the moment when the point where the value of (the length from the mouthpiece end to the gripping point)/(the total length) is 0.3 is gripped is 15.5 gf·cm or less, it is preferably the case that a value of (the length from the mouthpiece end 13A to the center of gravity)/(the total length) is in the range of 0.25 to 0.44. This numerical range corresponds to Examples A-2 to A-5, which are described later. According to this design, it is possible to position the center of gravity of the flavor aspirator 11 in the vicinity of a position where the value of (the length from the mouthpiece end 13A to the gripping point)/(the total length) is 0.3. It is thereby possible to realize the flavor aspirator 11 that is easy for the user to hold and causes less fatigue to the user when being gripped.

In this case, even more preferably, a value of (the length from the mouthpiece end 13A to the center of gravity)/(the total length) should fall within the range of 0.3 to 0.44. This numerical range corresponds to Examples A-3 to A-5, which are described later. According to this design, it is possible to position the center of gravity of the flavor aspirator 11 much closer to a position where the value of (the length from the mouthpiece end 13A to the gripping point)/(the total length) is 0.3. It is thereby possible to realize the flavor aspirator 11 that is easy for the user to hold and causes less fatigue to the user when being gripped.

The total weight of the flavor aspirator 11 is in the range of 10.4 g to 15.5 g. Preferably, the total weight of the flavor aspirator 11 is in the range of 10.4 g to 13.9 g. According to this design, it is possible to bring the weight of the flavor aspirator 11 into an appropriate range; in other words, to ensure that the flavor aspirator 11 is not too heavy, and to realize the flavor aspirator 11 that causes less fatigue to the user even when the user grips the aspirator 11 for a long time.

The weight-concentrated part is at least partially made of a metal. According to this design, it is easy to make the weight of the weight-concentrated part heavier than the other parts at the position where a value of (the length from the mouthpiece end 13A to the position)/(the total length) is in the vicinity of 0.3. It is thereby possible to realize the flavor aspirator 11 that is easy for the user to hold and causes less fatigue to the user when being gripped.

According to the present embodiment, the flavor aspirator 11 is of non-combustion type. According to this design, disadvantages caused by combustion can be avoided. It is thereby possible to realize the flavor aspirator 11 that is capable of generating flavors that the user prefers, without the use of fire.

In the following, the second through seventh embodiments, which are modifications of the first embodiment, will be described with reference to FIG. 2 to FIG. 7. In the following embodiments, the differences from the first embodiment will mainly be described, and descriptions of similarities with the first embodiment will be omitted.

Second Embodiment

A second embodiment of the flavor aspirator 11 will be described with reference to FIG. 2. In the present embodiment, the mouthpiece 13 and the first part 12A of the housing 12 are made of a resin such as polycarbonate, polyacetal, polypropylene, fluorine resin (Teflon (registered trademark)), for example. The wall thickness of the mouthpiece 13 is larger than that of the mouthpiece 13 of the first embodiment. The wall thickness of the first part 12A is larger than that of the first part 12A of the first embodiment. On the other hand, the wall thickness of the second part 12B of the housing 12 is thinner than that of the second part 12B of the first embodiment.

In the present embodiment, the mouthpiece 13 and the first part 12A both having a large wall thickness constitute a first weight-concentrated part 25. The first weight-concentrated part 25 is provided at a position off the mouthpiece end 13A and closer to the mouthpiece end 13A than a midpoint position 26 between the mouthpiece end 13A and the distal end 14. The first weight-concentrated part 25 accounts for at least approximately half of the total weight of the flavor aspirator 11. The center of gravity of the flavor aspirator 11 is set in such a manner that a value of (the length from the mouthpiece end 13A to the center of gravity)/(the total length) falls within the range of 0.20 to 0.45.

According to the present embodiment, the first weight-concentrated part 25 is located in the vicinity of the point gripped by the user, and the center of gravity of the flavor aspirator 11 is also located in the vicinity of the point gripped by the user. It is thereby possible to achieve the flavor aspirator 11 that can control generation of an acting moment to the extent that the installation angle of the flavor aspirator 11 is changed, and that can be easily held and causes less fatigue to the user.

Third Embodiment

Figure 3:
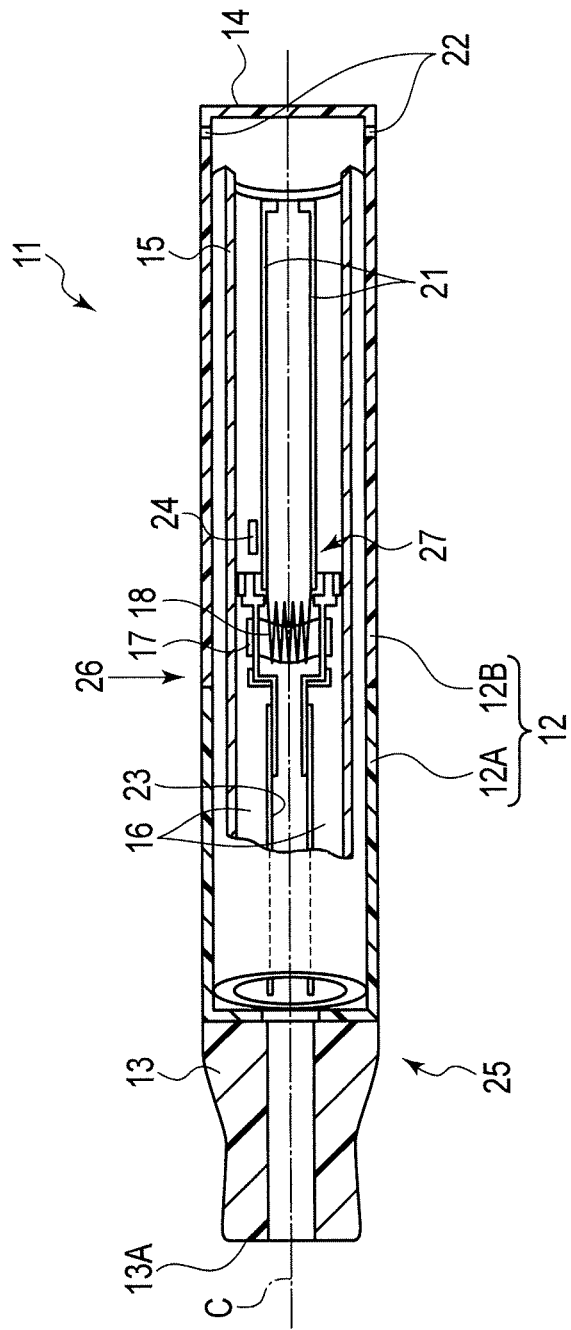
FIG. 3 is a cross-sectional view of a flavor aspirator of a third embodiment, taken along a plane including a central axis.

A third embodiment of the flavor aspirator 11 will be described with reference to FIG. 3. In the present embodiment, the mouthpiece 13 and the first part 12A of the housing 12 are made of a resin such as polycarbonate, polyacetal, polypropylene, fluorine resin (Teflon (registered trademark)), for example. The mouthpiece 13 and the first part 12A of the housing 12 may be made of a metal such as stainless steel or brass.

The battery 15 is formed in a cylindrical shape, and a storage 27 capable of storing various components is formed inside the battery 15. The battery 15 is not limited to a cylindrical shape; it may be formed by folding a sheet-like battery into a cylindrical shape, for example. FIG. 3 is a cutaway view of the cylindrical battery 15 to show the structure inside the storage 27. In the storage 27, the aerosol source 16, the wick 17, the heater 18, the wiring 21, and the ventilation path 23 are provided. Air-intake holes 22 are provided on the distal end 14 side, and the arrangement and shapes of the air-intake holes 22 are the same as those in the first embodiment.

The aerosol source 16 is arranged close to the mouthpiece end 13A side. In the present embodiment, the mouthpiece 13, the first part 12A, and the part of the battery 15 on the mouthpiece end 13A side constitute a first weight-concentrated part 25. The first weight-concentrated part 25 is provided at a position off the mouthpiece end 13A and closer to the mouthpiece end 13A than to a midpoint position 26 between the mouthpiece end 13A and the distal end 14. The first weight-concentrated part 25 accounts for at least approximately half of the total weight of the flavor aspirator 11. The center of gravity of the flavor aspirator 11 is set in such a manner that a value of (the length from the mouthpiece end 13A to the center of gravity)/(the total length) falls within the range of 0.20 to 0.45.

According to the present embodiment, the first weight-concentrated part 25 is located in the vicinity of the point gripped by the user, and the center of gravity of the flavor aspirator 11 is also located in the vicinity of the point gripped by the user. It is thereby possible to achieve the flavor aspirator 11 that can control generation of an acting moment to the extent that the installation angle of the flavor aspirator 11 is changed, and that can be easily held.

Fourth Embodiment

Figure 4:
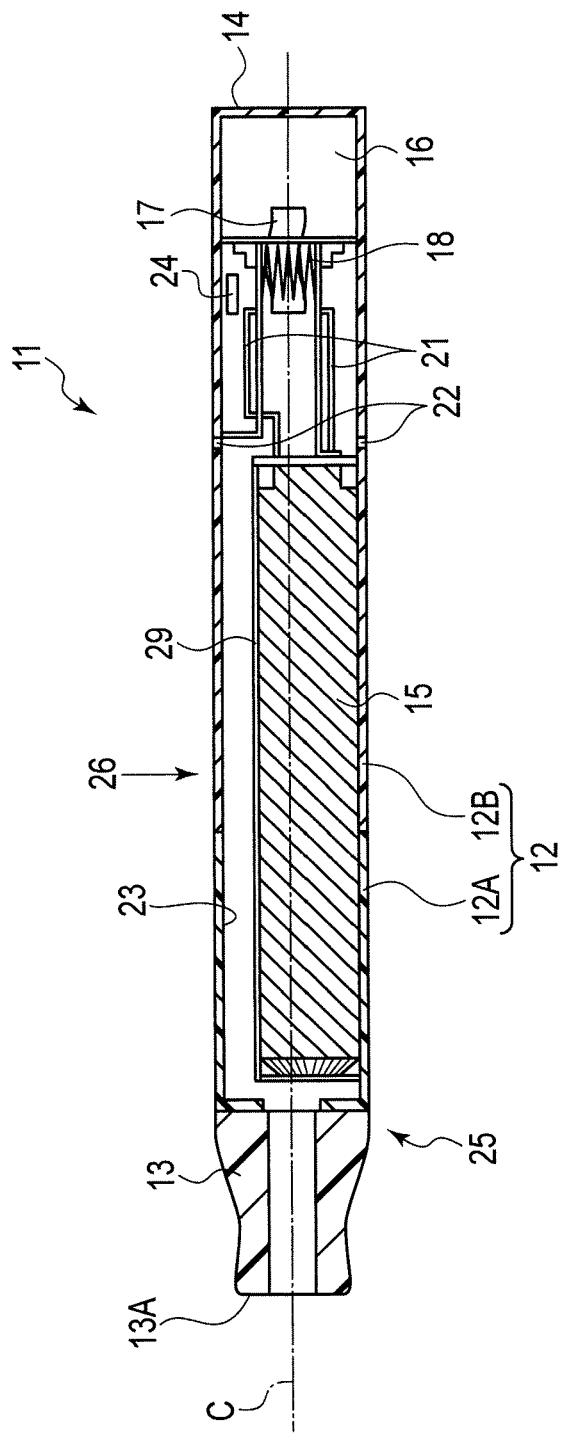
FIG. 4 is a cross-sectional view of a flavor aspirator of a fourth embodiment, taken along a plane including a central axis.

A fourth embodiment of the flavor aspirator 11 will be described with reference to FIG. 4. In the present embodiment, the battery 15 is designed to have a smaller length in the direction of the central axis C and a smaller diameter, compared to the battery 15 of the first embodiment, and the battery 15 is provided close to the mouthpiece end 13A side. A ventilation path 23 is formed so as to pass through the side of the battery 15, and a partition wall 29 is provided between the battery 15 and the ventilation path 23. The aerosol source 16 is provided close to the distal end 14 (to the most distal side).

The mouthpiece 13 and the first part 12A of the housing 12 are made of a resin such as polycarbonate, polyacetal, polypropylene, fluorine resin (Teflon (registered trademark)), for example. The mouthpiece 13 may be made of a metal such as stainless steel or brass.

The wick 17 and the heater 18 are provided at midpoint positions between the battery 15 and the aerosol source 16. Air-intake holes 22 are provided at positions between the battery 15 and the aerosol source 16, and the arrangement and shapes of the air-intake holes 22 are the same as those in the first embodiment.

In the present embodiment, the battery 15 and the mouthpiece 13 constitute a first weight-concentrated part 25. The first weight-concentrated part 25 is provided at a position off the mouthpiece end 13A, and closer to the mouthpiece end 13A than to a midpoint position 26 between the mouthpiece end 13A and the distal end 14. The first weight-concentrated part 25 accounts for at least approximately half of the total weight of the flavor aspirator 11. The center of gravity of the flavor aspirator 11 is set in such a manner that a value of (the length from the mouthpiece end 13A to the center of gravity)/(the total length) falls within the range of 0.20 to 0.45.

According to the present embodiment, the first weight-concentrated part 25 is located in the vicinity of the point gripped by the user, and the center of gravity of the flavor aspirator 11 is also located in the vicinity of the point gripped by the user. It is thereby possible to achieve the flavor aspirator 11 that can control generation of an acting moment to the extent that the installation angle of the flavor aspirator 11 is changed, and that it can be easily held.

Fifth Embodiment

Figure 5:
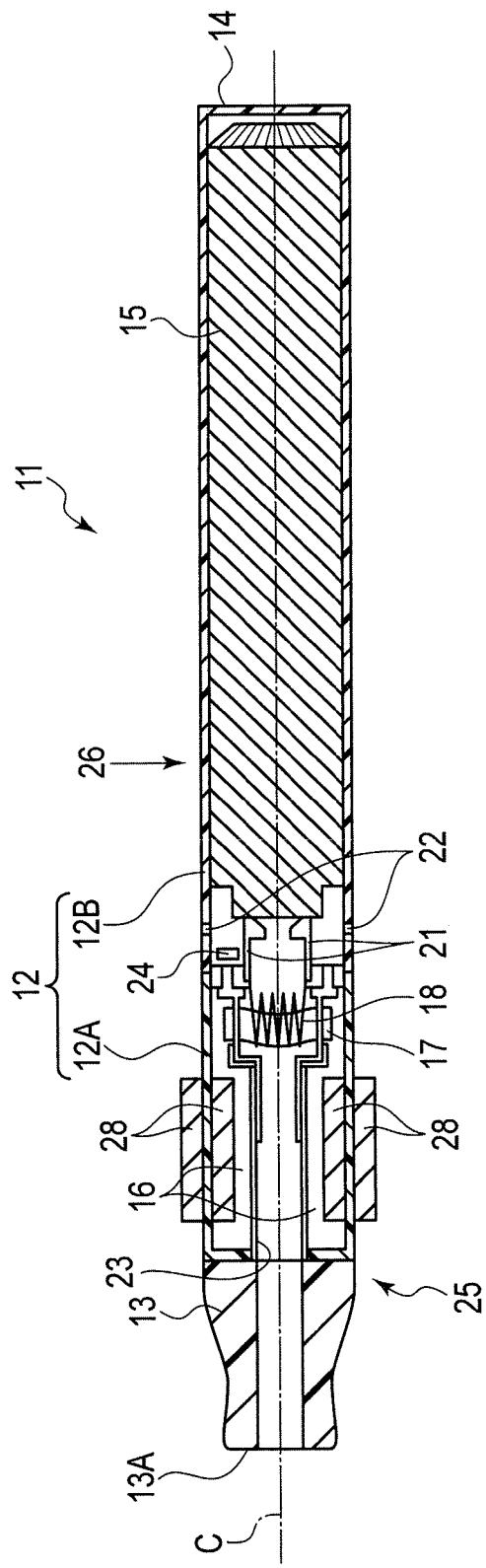
FIG. 5 is a cross-sectional view of a flavor aspirator of a fifth embodiment, taken along a plane including a central axis.

A fifth embodiment of the flavor aspirator 11 will be described with reference to FIG. 5. A weight-adjustment member 28 (weight) is provided in the first part 12A of the housing 12. The member 28 is made of a metallic material such as stainless steel or brass. In the present embodiment, the member 28 is provided on both the inner side and the outer side of the first part 12A. The member 28 may be provided either inside or outside of the first part 12A. The mouthpiece 13 and the first part 12A of the housing 12 are made of a resin such as polycarbonate, polyacetal, polypropylene, fluorine resin (Teflon (registered trademark)), for example. The mouthpiece 13 may be made of a metal such as stainless steel or brass.

In the present embodiment, the weight-adjustment member 28, the mouthpiece 13, and the aerosol source 16 constitute a first weight-concentrated part 25. The first weight-concentrated part 25 is provided at a position off the mouthpiece end 13A, and closer to the mouthpiece end 13A than to a midpoint position 26 between the mouthpiece end 13A and the distal end 14. The first weight-concentrated part 25 accounts for at least approximately half of the total weight of the flavor aspirator 11. The center of gravity of the flavor aspirator 11 is set in such a manner that a value of (the length from the mouthpiece end 13A to the center of gravity)/(the total length) falls within the range of 0.20 to 0.45.

According to the present embodiment, the weight-concentrated part has the weight-adjustment member 28. According to this design, the weight of the first weight-concentrated part 25 can be changed relatively easily, and the flavor aspirator 11 can be easily designed. According to the present embodiment, the first weight-concentrated part 25 is arranged in the vicinity of the point gripped by the user, and the center of gravity of the flavor aspirator 11 is also located in the vicinity of the point gripped by the user. It is thereby possible to achieve the flavor aspirator 11 that can control generation of an acting moment to the extent that the installation angle of the flavor aspirator 11 is changed, and that it can be easily held and cause less fatigue to the user.

Sixth Embodiment

Figure 6:
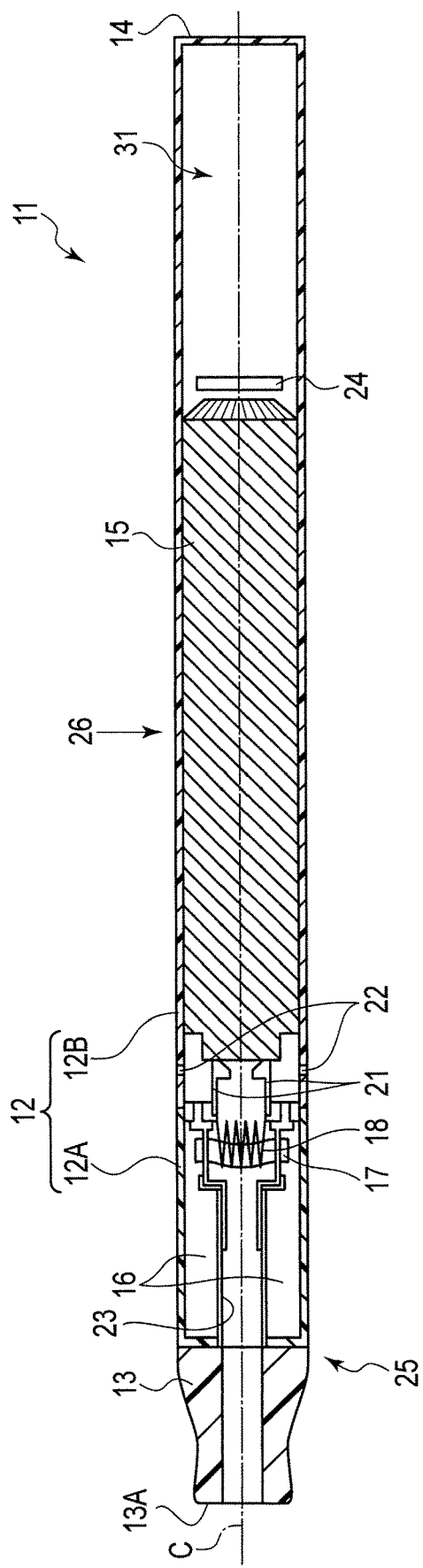
FIG. 6 is a cross-sectional view of a flavor aspirator of a sixth embodiment, taken along a plane including a central axis.

A sixth embodiment of the flavor aspirator 11 will be described with reference to FIG. 6. In the present embodiment, the housing 12 is formed so as to be longer in the axial direction (the direction of the center axis C) compared to the housing 12 in the first embodiment. For this reason, the battery 15 is arranged close to the mouthpiece end 13A side with respect to the entire housing 12. The mouthpiece 13 and the first part 12A of the housing 12 are made of a resin such as polycarbonate, polyacetal, polypropylene, fluorine resin (Teflon (registered trademark)), for example. The mouthpiece 13 may be made of a metal such as stainless steel or brass. On the inside of the housing 12, a hollow part 31 is formed on the distal end 14 side. The drive circuit 24 is formed as a disk-shaped substrate and is provided in the hollow part 31.

In the present embodiment, the part of the battery 15 on the mouthpiece end 13A side, the mouthpiece 13, and the aerosol source 16 constitute a first weight-concentrated part 25. The first weight-concentrated part 25 is provided at a position off of the mouthpiece end 13A and closer to the mouthpiece end 13A than to a midpoint position 26 between the mouthpiece end 13A and the distal end 14. The first weight-concentrated part 25 accounts for at least approximately half of the total weight of the flavor aspirator 11. The center of gravity of the flavor aspirator 11 is set in such a manner that a value of (the length from the mouthpiece end 13A to the center of gravity)/(the total length) falls within the range of 0.20 to 0.45.

According to the present embodiment, the first weight-concentrated part 25 is located in the vicinity of the point gripped by the user, and the center of gravity of the flavor aspirator 11 is also located in the vicinity of the point gripped by the user. It is thereby possible to achieve the flavor aspirator 11 that can reduce generation of an acting moment to the extent that the installation angle of the flavor aspirator 11 is changed, and that can be easily held and cause less fatigue to the user.

Seventh Embodiment

Figure 7:
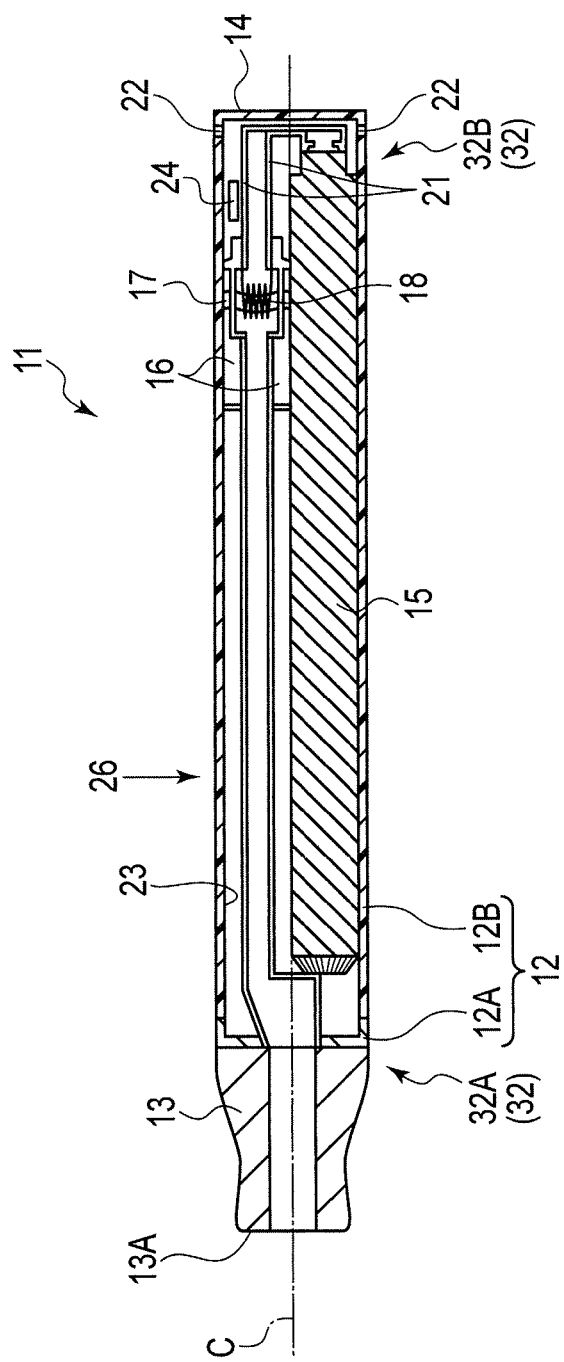
FIG. 7 is a cross-sectional view of a flavor aspirator of a seventh embodiment, taken along a plane including a central axis.

A seventh embodiment of the flavor aspirator 11 will be described with reference to FIG. 7. In the present embodiment, the cross-sectional area of the battery 15 taken along the direction intersecting the direction of the central axis C is smaller than that in the first embodiment. The battery 15 is provided in parallel with the ventilation path 23, the aerosol source 16, the wick 17, the wiring 21, and the heater 18. The mouthpiece 13 and the first part 12A of the housing 12 are made of a metal such as stainless steel or brass.

In the present embodiment, the mouthpiece 13, the part of the battery 15 on the mouthpiece end 13A side, the part of the battery 15 on the distal end 14 side, the aerosol source 16, the wick 17, and the heater 18 constitute a second weight-concentrated part 32. The second weight-concentrated part 32 is in a position different from the position of the foregoing first weight-concentrated part 25 with respect to the direction of the central axis C. The second weight-concentrated part 32 consists of a part 32A in the vicinity of the mouthpiece end and a part 32B in the vicinity of the distal end. The part 32A in the vicinity of the mouthpiece end is constituted by a part where a value of (the length from the mouthpiece end 13A to the part)/(the total length) is in the range of 0 to 0.2. The part 32A in the vicinity of the mouthpiece end consists of, for example, the mouthpiece 13 made of a metal, and a part of the battery 15 on the mouthpiece end 13A side.

The part 32B in the vicinity of the distal end is constituted by a part where a value of (the length from the mouthpiece end 13A to the part)/(the total length) is in the range of 0.9 to 1.0. The part 32B in the vicinity of the distal end consists of, for example, the aerosol source 16, the wick 17, the heater 18, and a part of the battery 15 on the distal end 14 side. Preferably, the weight of the part 32A in the vicinity of the mouthpiece end should be heavier than the weight of the part 32B in the vicinity of the distal end.

In the second weight-concentrated part 32, a sum of the weight of the part 32A in the vicinity of the mouthpiece end and the weight of the part 32B in the vicinity of the distal end accounts for about at least half of the total weight of the flavor aspirator 11. More specifically, in the second weight-concentrated part 32, a sum of the weight of a part where a value of (the length from the mouthpiece end to the part)/(the total length) is in the range of 0 to 0.2, and the weight of a part where a value of (the length from the mouthpiece end to the part)/(the total length) is in the range of 0.9 to 1.0 accounts for 45% or more of the total weight of the flavor aspirator 11. Preferably, the weight of the second weight-concentrated part 32 accounts for 50% or more but not more than 86% of the total weight of the flavor aspirator 11.

In the present embodiment, the absolute value of a moment when the point where the value of (the length from the mouthpiece end 13A to the point)/(the total length) is 0.3 is gripped by hand (fingers) is set to be 20.0 gf·cm or less. Preferably, the absolute value of a moment is set to be 14.5 gf·cm or less. On the other hand, the absolute value of a moment can also be set to 11.25 gf·cm or less as described later.

The center of gravity of the flavor aspirator 11 is set in such a manner that a value of (the length from the mouthpiece end 13A to the center of gravity)/(the total length) falls within the range of 0.20 to 0.45. Preferably, the position of the center of gravity is set in such a manner that a value of (the length from the mouthpiece end 13A to the center of gravity)/(the total length) falls within the range of 0.25 to 0.44. Even more preferably, the position of the center of gravity is set in such a manner that a value of (the length from the mouthpiece end 13A to the center of gravity)/(the total length) falls within the range of 0.3 to 0.44.

In the present embodiment, the second weight-concentrated part 32 is distributed in the part 32A in the vicinity of the mouthpiece end, and in the part 32B in the vicinity of the distal end, and the center of gravity of the flavor aspirator 11 is located in the vicinity of the gripping point. Thus, when the flavor aspirator 11 is substantially gripped, for example, horizontally with fingers, the second weight-concentrated part 32 distributed in two places allows a user to easily balance the flavor aspirator 11, and an acting moment to the extent that the installation angle of the flavor aspirator 11 is changed can be reduced.

According to the present embodiment, the flavor aspirator 11 extends from the mouthpiece end 13A to the distal end in a rod-like or columnar shape, and has a weight-concentrated part that is distributed in the part 32A in the vicinity of the mouthpiece end, and in the part 32B in the vicinity of the distal end, and that has a weight accounting for at least about half of the total weight, the weight being a sum of the weight of the part 32A and the weight of the part 32B, and has a value of (the length from the mouthpiece end 13A to the center of gravity)/(the total length) within the range of 0.20 to 0.45. More specifically, in the second weight-concentrated part 32, a sum of the weight of a part where a value of (the length from the mouthpiece end to the part)/(the total length) is in the range of 0 to 0.2 and the weight of a part where the value of (the length from the mouthpiece end to the part)/(the total length) is in the range of 0.9 to 1.0, accounts for 45% or more of total weight of the flavor aspirator 11. Preferably, the weight of the second weight-concentrated part 32 accounts for 50% or more and no more than 86% of the total weight of the flavor aspirator 11.

As a result of having conducted user surveys, the inventors found that the users in the act of smoking grip the vicinity of the position where the value of (the length from the mouthpiece end 13A to the position)/(the total length) is 0.3. According to this design, it is possible to position the center of gravity of the flavor aspirator 11 at a position where the value of (the length from the mouthpiece end 13A to the position)/(the total length) is in the vicinity of 0.3. The second weight-concentrated part 32 is provided in the part 32A in the vicinity of the mouthpiece end, and in the part 32B in the vicinity of the distal end. Thus, when gripping the flavor aspirator 11 with fingers, for example, in a substantially horizontal direction, the user can easily balance the flavor aspirator with the second weight-concentrated part 32 distributed in two places; that is, in the mouthpiece end 13A side and in the distal end 14 side. Furthermore, it is possible to reduce an acting moment to the extent that the installation angle of the flavor aspirator 11 is changed. It is thereby possible to achieve the flavor aspirator 11 that is easy to hold and causes less fatigue when being gripped.

Preferably, the absolute value of the moment when the point where the value of (the length from the mouthpiece end to the point)/(the total length) is 0.3 should be gripped is 14.5 gf·cm or less. This numerical range corresponds to Examples B-2 to B-6, which are described later. According to this design, it is thereby possible to achieve the flavor aspirator 11 that can reduce an acting moment to the extent that the installation angle of the flavor aspirator 11 is changed when the flavor aspirator 11 is gripped, and that is easy for the user to hold and causes less fatigue to the user.

In the case where the absolute value of the moment is 14.5 gf·cm or less when the part where the value of (the length from the mouthpiece end to the part)/(the total length) is 0.3, a value of (the length from the mouthpiece end 13A to the center of gravity)/(the total length) is preferably in the range of 0.25 to 0.44. This numerical range corresponds to Examples B-3 to B-6, which are described later. According to this design, it is possible to position the center of gravity of the flavor aspirator 11 much closer to a position where the value of (the length from the mouthpiece end 13A to the gripping position)/(the total length) is 0.3. It is thereby possible to realize the flavor aspirator 11 that is easy for the user to hold and causes less fatigue to the user when being gripped.

In this case, more preferably, a value of (the length from the mouthpiece end 13A to the center of gravity)/(the total length) falls within the range of 0.3 to 0.44. This numerical range corresponds to Examples B-4 to B-6, which are described later. According to this design, it is possible to position the center of gravity of the flavor aspirator 11 much closer to a position where the value of (the length from the mouthpiece end 13A to the gripping position)/(the total length) is 0.3. It is thereby possible to realize the flavor aspirator 11 that is easy for the user to hold and causes less fatigue to the user when being gripped.

Figure 8:
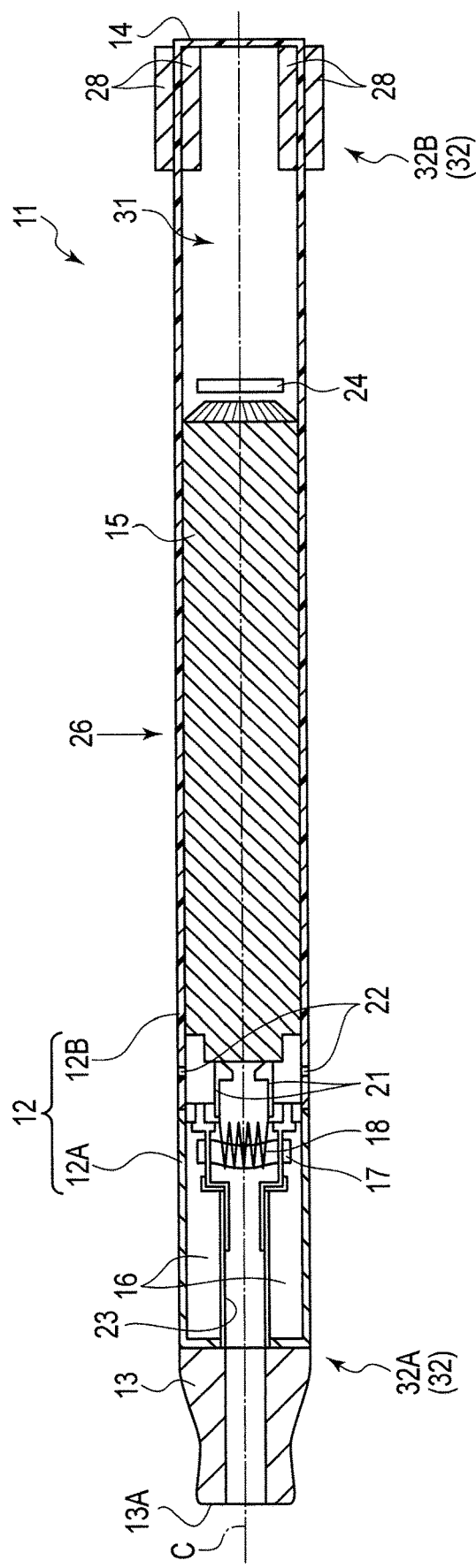
FIG. 8 is a cross-sectional view of a flavor aspirator of an eighth embodiment, taken along a plane including a central axis.
Figure 9:
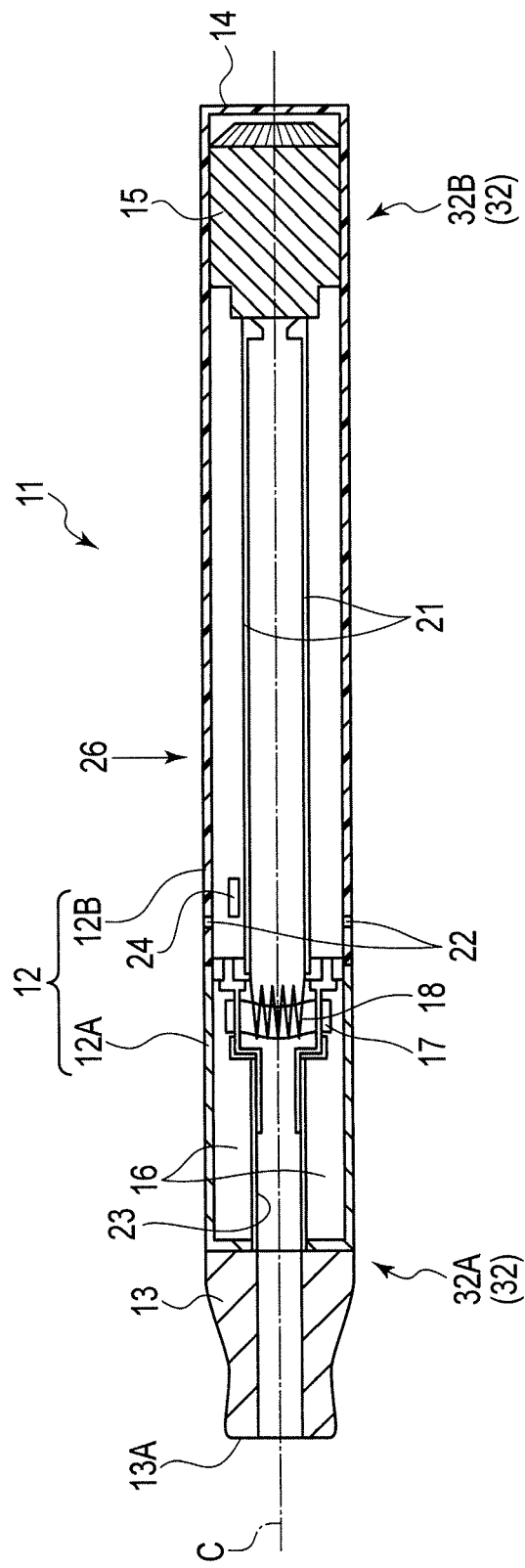
FIG. 9 is a cross-sectional view of a flavor aspirator of a ninth embodiment, taken along a plane including a central axis.

Here, the eighth through tenth embodiments, which are modifications of the seventh embodiment, will be described with reference to FIG. 8 to FIG. 10. In the following embodiments, the differences from the seventh embodiment will mainly be described, and descriptions of similarities with the seventh embodiment will be omitted.

Eighth Embodiment

An eighth embodiment of the flavor aspirator 11 will be described with reference to FIG. 8. In the present embodiment, the housing 12 is formed so as to be longer in the axial direction (the direction of the center axis C) than that in the first embodiment. The battery 15 is provided at a midpoint position 26 in the direction of the central axis C of the housing 12. A weight-adjustment member 28 (weight) is provided in the distal end 14 side of the housing 12 (the second part 12B). The member 28 is made of a metallic material such as stainless steel or brass. In the present embodiment, the member 28 is provided on both the inner side and the outer side of the second part 12B. The member 28 may be provided either inside or outside of the second part 12B. The mouthpiece 13 and the first part 12A of the housing 12 are made of a metal such as stainless steel or brass.

The mouthpiece 13, the aerosol source 16, the wick 17, the heater 18, and the part of the battery 15 on the mouthpiece end 13A side constitute a part 32A of the second weight-concentrated part 32 in the vicinity of the mouthpiece end. The weight-adjustment member 28 constitutes a part 32B of the second weight-concentrated part 32 in the vicinity of the distal end. In the second weight-concentrated part 32, a sum of the weight of the part 32A in the vicinity of the mouthpiece end and the weight of the part 32B in the vicinity of the distal end accounts for at least about half of the total weight of the flavor aspirator 11.

In the present embodiment, the center of gravity of the flavor aspirator 11 is set in such a manner that a value of (the length from the mouthpiece end 13A to the center of gravity)/(the total length) falls within the range of 0.20 to 0.45.

According to the present embodiment, the weight-adjustment member 28 is provided in a part where a value of (the length from the mouthpiece end 13A to the part)/(the total length) is in the range of 0.9 to 0.1. According to this design, the weight of the second weight-concentrated part 32 can be changed relatively easily, and the design of the flavor aspirator 11 can be easily performed. Furthermore, according to the present embodiment, the second weight-concentrated part 32 is distributed in two places, namely the mouthpiece end 13A side and the distal end 14 side, and the center of gravity of the flavor aspirator 11 is located in the vicinity of the point gripped by the user. Thus, it is easy to balance the flavor aspirator 11 with the second weight-concentrated part 32 distributed in two places, namely the mouthpiece end 13A side and the distal end 14 side, and it is possible to reduce an acting moment to the extent that the installation angle of the flavor aspirator 11 is changed. It is thereby possible to realize the flavor aspirator 11 that is easy for the user to hold and causes less fatigue to the user when being gripped.

Ninth Embodiment

A ninth embodiment of the flavor aspirator 11 will be described with reference to FIG. 9. In the present embodiment, the battery 15 is formed so as to be shorter in the direction of the central axis C and to be smaller in size, compared to the battery in the foregoing embodiments. The battery 15 is provided inside the housing 12 at a position close to the distal end 14 side. The mouthpiece 13 and the first part 12A of the housing 12 are made of a metal such as stainless steel or brass.

The mouthpiece 13, the first part 12A of the housing 12, the aerosol source 16, the wick 17, and the heater 18 constitute a part 32A of the second weight-concentrated part 32 in the vicinity of the mouthpiece end. The battery 15 constitutes a part 32B in the vicinity of the distal end of the second weight-concentrated part 32. In the second weight-concentrated part 32, a sum of the weight of the part 32A in the vicinity of the mouthpiece end and the weight of the part 32B in the vicinity of the distal end accounts for at least about half of the total weight of the flavor aspirator 11.

In the present embodiment, the center of gravity of the flavor aspirator 11 is set in such a manner that a value of (the length from the mouthpiece end 13A to the center of gravity)/(the total length) falls within the range of 0.20 to 0.45.

According to the present embodiment, the second weight-concentrated part 32 is distributed in two places, namely the mouthpiece end 13A side and the distal end 14 side, and the center of gravity of the flavor aspirator 11 is located in the vicinity of the point gripped by the user. Thus, it is easy to balance the flavor aspirator 11 with the second weight-concentrated part 32 distributed in two places, namely the mouthpiece end 13A side and the distal end 14 side, and it is possible to reduce an acting moment to the extent that the installation angle of the flavor aspirator 11 is changed. It is thereby possible to realize the flavor aspirator 11 that is easy for the user to hold and causes less fatigue to the user when being gripped.

10th Embodiment

A tenth embodiment of the flavor aspirator 11 will be described with reference to FIG. 10. The battery 15 is provided in the vicinity of a midpoint position 26 in the direction of the central axis C of the housing 12. A weight-adjustment member 28A (weight) is provided in the mouthpiece end 13A side of the housing 12 (the first part 12A). A weight-adjustment member 28B (weight) is provided in the distal end side of the housing 12 (the second part 12B). The members 28A and 28B are made of a metallic material such as stainless steel or brass. In the present embodiment, the members 28A and 28B are provided on both the inner side and the outer side of the first part 12A, and on both the inner side and the outer side of the second part 12B. The member 28A may be provided either inside or outside of the first part 12A. The member 28B may be provided either inside or outside of the second part 12B. In the case where the member 28B is provided only on the outer side of the second part 12B, the battery 15 may occupy the inside of the housing 12, up to the distal end 14 (such that there is no space on the distal end side of the housing 12). In the present embodiment, both the member 28A and the member 28B are provided, but only one of them may actually be provided. The mouthpiece 13 and the first part 12A of the housing 12 are made of a metal such as stainless steel or brass.

The mouthpiece 13, the aerosol source 16, the wick 17, the heater 18, and the member 28A constitute a part 32A in the vicinity of the mouthpiece end of the second weight-concentrated part 32. The member 28B constitutes a part 32B in the vicinity of the distal end of the second weight-concentrated part 32. In the second weight-concentrated part 32, a sum of the weight of the part 32A in the vicinity of the mouthpiece end and the weight of the part 32B in the vicinity of the distal end accounts for at least about half of the total weight of the flavor aspirator 11. In the present embodiment, the center of gravity of the flavor aspirator 11 is set in such a manner that a value of (the length from the mouthpiece end 13A to the center of gravity)/(the total length) falls within the range of 0.20 to 0.45.

According to the present embodiment, the weight of the second weight-concentrated part 32 can be changed relatively easily, and the design of the flavor aspirator 11 can be easily performed. Furthermore, according to the present embodiment, the second weight-concentrated part 32 is distributed in two places, namely the mouthpiece end 13A side and the distal end 14 side, and the center of gravity of the flavor aspirator 11 is located in the vicinity of the point gripped by the user. Thus, it is easy to balance the flavor aspirator 11 with the second weight-concentrated part 32 distributed in two places, namely the mouthpiece end 13A side and the distal end 14 side, and it is possible to reduce an acting moment to the extent that the installation angle of the flavor aspirator 11 is changed. It is thereby possible to realize the flavor aspirator 11 that is easy for the user to hold and causes less fatigue to the user when being gripped.

11th Embodiment

An 11th embodiment of the flavor aspirator 11 will be described with reference to FIG. 11. In the present embodiment, the differences from the first embodiment or the seventh embodiment will mainly be described, and descriptions of similarities with the first embodiment will be omitted.

Figure 11:
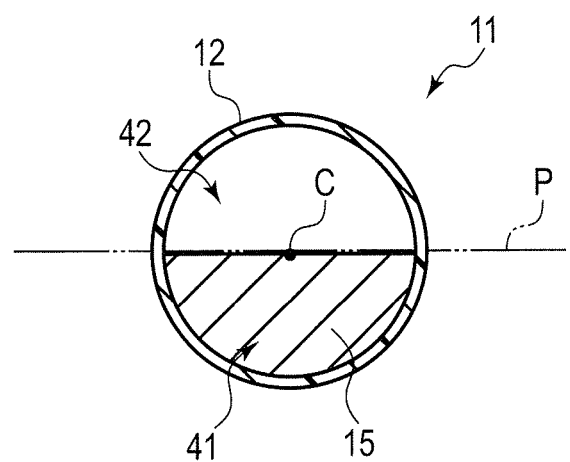
FIG. 11 is a cross-sectional view of a flavor aspirator of an 11th embodiment, taken along a plane including a central axis.

As shown in FIG. 11, in the present embodiment, the battery 15 has a substantially semicircular cross-sectional shape when cut at a plane intersecting the central axis C. For this reason, in the present embodiment, when the flavor aspirator 11 is divided by the plane P including the central axis C, the weight of the divided segment 41 is heavier than the weight of the other divided segment 42. Specifically, the weight of the divided segment 41 of the flavor aspirator 11 is 1.5 times heavier than the weight of the other divided segment 42. More specifically, the weight of the divided segment 41 of the flavor aspirator 11 is preferably heavier by 1.5 times or more and not more than 10 times than the weight of the other divided segment 42. Even more preferably, the weight of the divided segment 41 of the flavor aspirator 11 should be heavier by 1.5 times or more and not more than 5 times than the weight of the other divided segment 42.

According to the present embodiment, when the flavor aspirator 11 is divided by a plane passing through the central axis C extending from the mouthpiece end 13A to the distal end 14, the weight of the divided segment 41 is 1.5 times heavier than the weight of the divided other segment 42. According to this design, the flavor aspirator 11 causes imbalance in weights between the divided segment 41 and the other divided segment 42 obtained by dividing the flavor aspirator 11 by the plane including the center axis C. If the flavor aspirator 11 is made in a cylindrical shape, it is thus possible to prevent the flavor aspirator 11 from rolling on a desk, etc. This makes it possible to reduce the risk of damaging the internal electronic components of the flavor aspirator 11 due to the fall of the flavor aspirator 11 from the desk. Furthermore, for example, if a power-activation switch is provided in the housing 12 on the other divided segment 42 side, it is possible to design the flavor aspirator 11 in such a manner that the switch always comes on the upper side, thereby providing good usability.

In the present embodiment, the battery 15 has a substantially semicircular cross-sectional shape, thereby causing imbalance in weights between the divided segment 41 and the other segment 42; however, a method of causing imbalance in weights is not limited thereto. For example, imbalance in weights may be caused by arranging, inside the housing 12, a weight-adjustment member (weight) having a substantially semicircular cross-sectional shape or a flexible sheet-like member (weight) bent to form a substantially semicircular shape. This also prevents the columnar flavor aspirator 11 from rolling on the desk, etc. and falling therefrom.

The flavor aspirator 11 is not limited to the foregoing embodiments described above; the flavor aspirator 11 can be realized by modifying the structural elements without departing from the gist of the invention when flavor aspirator 11 is implemented. For example, the housing 12 is not limited to a cylindrical shape, and may alternatively be formed into a tubular shape having a rectangular cross section. In addition, it is possible to realize one flavor aspirator 11 by appropriately combining the constituent elements in the foregoing different embodiments.

EXAMPLES

Figure 13:
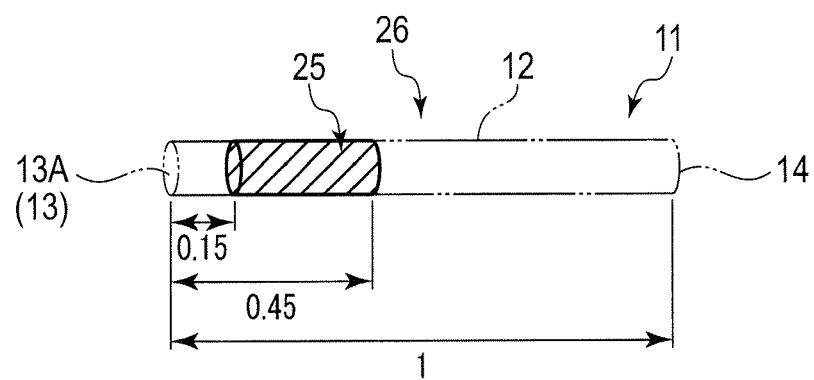
FIG. 13 is a schematic view showing a concept of a flavor aspirator of Examples A-1 to A-6.

Hereinafter, examples of the flavor aspirator 11 will be described with reference to FIGS. 12 to 17. FIG. 12 shows the conditions of each of the sub-examples of Example A, the sub-examples of Example B, a conventional product, and comparative examples. FIG. 13 is a conceptual diagram of Example A, and Example A corresponds to the foregoing first to sixth embodiments and eleventh embodiment. As shown in FIG. 13, in Examples A-1 to A-6 and Comparative Example A-7, a first weight-concentrated part 25 is provided in a position off the mouthpiece, and closer to the mouthpiece end 13A side than to the midpoint position 26 between the mouthpiece end 13A and the distal end 14. More specifically, the first weight-concentrated part 25 is provided at a position where a value of (the length from the mouthpiece end 13A)/(the total length) falls within the range of 0.15 to 0.45.

Figure 14:
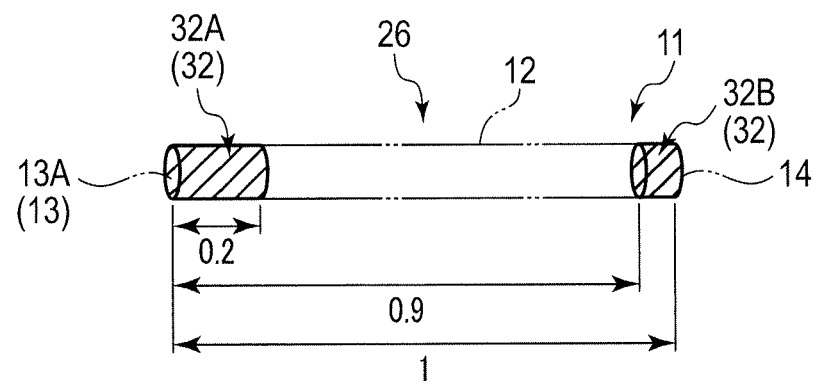
FIG. 14 is a schematic view showing a concept of a flavor aspirator of Examples B-1 to B-7.

FIG. 14 is a conceptual diagram of Example B, and Example B corresponds to the foregoing seventh-to-tenth embodiments and eleventh embodiment. As shown in FIG. 14, in Comparative Example B-1, Examples B-2 to B-7, and Comparative Example B-8, a second weight-concentrated part 32 is distributed in a part 32A in the vicinity of the mouthpiece end, and in a part 32B in the vicinity of the distal end. More specifically, the second weight-concentrated part 32 is distributed in two places, namely a position where a value of (the length from the mouthpiece end 13A to the position)/(the total length) is in the range of 0 to 0.2, and a position where the value is in the range of 0.9 to 1.0.

(Conventional Product 1)

Figure 15:
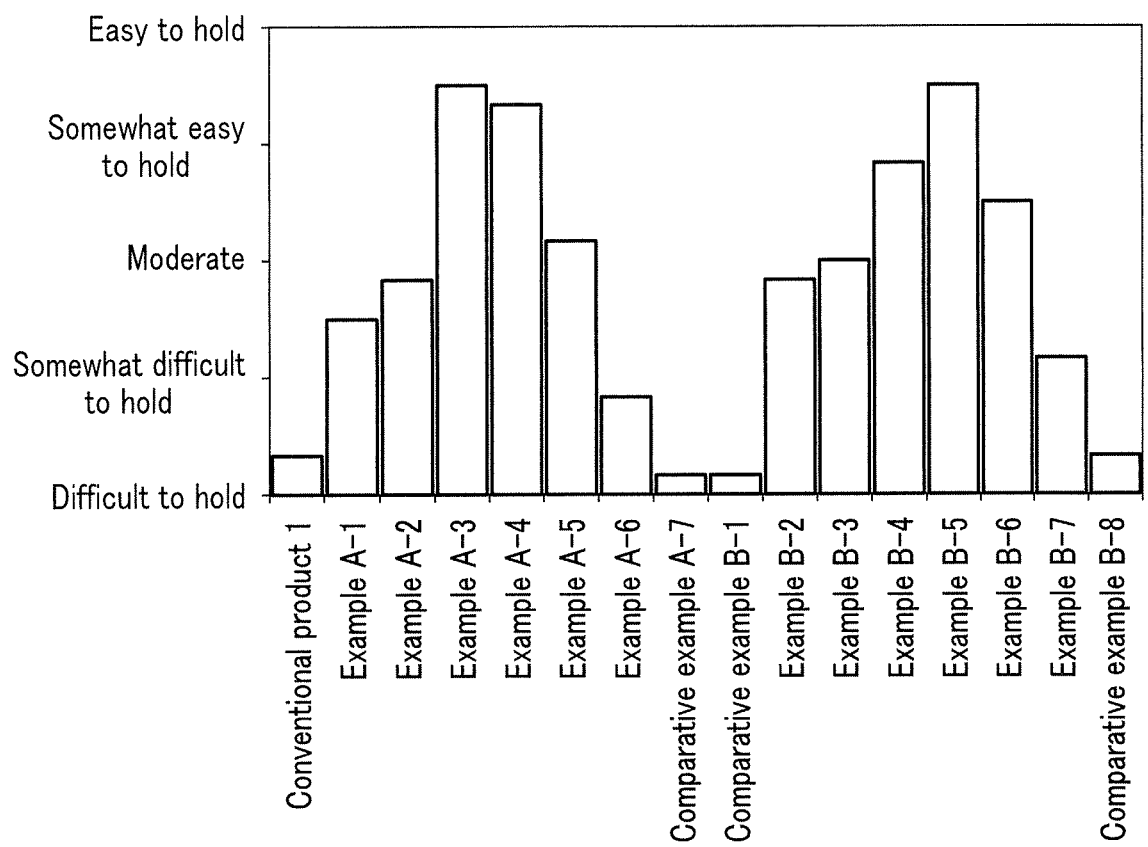
FIG. 15 is a graph showing results of sensory evaluations for ease of holding in each of the examples, the comparative examples, and the conventional product listed in FIG. 12.

The conventional product 1 has specifications as shown in the table shown in FIG. 12. The value of (the length from the mouthpiece end 13A to the center of gravity)/(the total length) is 0.52. Accordingly, the center of gravity of the conventional product 1 is located substantially in the vicinity of the midpoint position 26 in the direction of the central axis C of the flavor aspirator 11. The moment when the point where the value of (the length from the mouthpiece end 13A to the point)/(the total length) is 0.3 is gripped is 53.5 gf·cm. For this reason, since a relatively large moment is generated in the conventional product 1, it tends to be difficult for the user to hold the conventional product 1. This tendency was also supported by the result of the sensory evaluation obtained by evaluating (scoring) the ease of holding at times when a plurality of subjects actually gripped the conventional product 1. In this sensory evaluation, a score of 0 is given to the situation "difficult to hold", a score of 1 to "somewhat difficult to hold", a score of 2 to "moderate", a score of 3 to "somewhat easy to hold" and a score of 4 to "easy to hold". FIG. 15 shows the average score of six subjects, a mix of male and female. As a result, in the conventional product 1, the average point was positioned between "somewhat difficult to hold" and "difficult to hold" at a position closer to "difficult to hold". This result shows that the conventional product 1, evaluated as "difficult to hold," is actually the flavor aspirator 11.

Example A-1

In Example A-1, the weight of the first weight-concentrated part 25 accounts for 46% of the total weight of the flavor aspirator 11. In Example A-1, the position of the center of gravity is set in such a manner that the value of (the length from the mouthpiece 13 to the center of gravity)/(the total length) is 0.22.

In Example A-1, the moment when the point where the value of (the length from the mouthpiece end 13A to the point)/(the total length) is 0.3 is gripped is −11.8 gf·cm.

As shown in FIG. 15, a score of the sensory evaluation result in Example A-1 was about halfway between "moderate" and "somewhat difficult to hold". For this reason, the ease of holding was evaluated as below "moderate".

Example A-2

In Example A-2, the weight of the first weight-concentrated part 25 accounts for 55% of the total weight of the flavor aspirator 11. In Example A-2, the position of the center of gravity is set in such a manner that the value of (the length from the mouthpiece end 13A to the center of gravity)/(the total length) is 0.25.

In Example A-2, the moment when the point where the value of (the length from the mouthpiece end 13A to the point)/(the total length) is 0.3 is gripped is −6.4 gf·cm.

As shown in FIG. 15, the sensory evaluation result in Example A-2 was between "moderate" and "somewhat difficult to hold", and somewhat close to "moderate". Accordingly, ease of holding was evaluated as generally "moderate".

Example A-3

In Example A-3, the weight of the first weight-concentrated part 25 accounts for 72% of the total weight of the flavor aspirator 11. In Example A-3, the position of the center of gravity is set in such a manner that the value of (the length from the mouthpiece end 13A to the center of gravity)/(the total length) is 0.3.

In Example A-3, the moment when the point where the value of (the length from the mouthpiece end 13A to the point)/(the total length) is 0.3 is gripped is 0.0 gf·cm. For this reason, in Example A-3, the moment is not generated when the point where the value of (the length from the mouthpiece end 13A)/(the total length) is 0.3 is gripped.

As shown in FIG. 15, a score of the sensory evaluation result in Example A-3 was about halfway between "easy to hold" and "somewhat easy to hold". Accordingly, ease of holding of the flavor aspirator 11 was evaluated as "easy to hold".

Example A-4

In Example A-4, the weight of the first weight-concentrated part 25 accounts for 82% of the total weight of the flavor aspirator 11. In Example A-4, the position of the center of gravity is set so that the value of (the length from the mouthpiece end 13A to the center of gravity)/(total length) is 0.35.

In Example A-4, the moment when the point where the value of (the length from the mouthpiece end 13A to the point)/(the total length) is 0.3 is gripped is 6.2 gf·cm.

As shown in FIG. 15, a score of the sensory evaluation result in Example A-4 was about halfway between "easy to hold" and "somewhat easy to hold". Accordingly, ease of holding of the flavor aspirator 11 was evaluated as "easy to hold".

Example A-5

In Example A-5, the weight of the first weight-concentrated part 25 accounts for 50% of the total weight of the flavor aspirator 11. In Example A-5, the position of the center of gravity is set in such a manner that the value of (the length from the mouthpiece end 13A to the center of gravity)/(the total length) is 0.44.

In Example A-5, the moment when the point where the value of (the length from the mouthpiece end 13A)/(the total length) is 0.3 is gripped is 14.5 gf·cm.

As shown in FIG. 15, a score of the sensory evaluation result in Example A-5 was about halfway between "somewhat easy to hold" and "moderate". Accordingly, ease of holding of the flavor aspirator 11 was evaluated as better than "moderate".

Example A-6

In Example A-6, the weight of the first weight-concentrated part 25 accounts for 50% of the total weight of the flavor aspirator 11. In Example A-6, the position of the center of gravity is set in such a manner that the value of (the length from the mouthpiece end 13A to the center of gravity)/(the total length) is 0.42.

In Example A-6, the moment when the point where the value of (the length from the mouthpiece end 13A)/(the total length) is 0.3 is gripped is 18.6 gf·cm.

As shown in FIG. 15, a score of the sensory evaluation result of Example A-6 was about halfway between "somewhat difficult to hold" and "difficult to hold". Accordingly, ease of holding of the flavor aspirator 11 was evaluated as poorer than "moderate".

Comparative Example A-7

In Example A-7, the weight of the first weight-concentrated part 25 accounts for 20% of the total weight of the flavor aspirator 11. In Example A-7, the position of the center of gravity is set in such a manner that the value of (the length from the mouthpiece end 13A to the center of gravity)/(the total length) is 0.52.

In Example A-7, the moment when the point where the value of (the length from the mouthpiece end 13A)/(the total length) is 0.3 is gripped is 34.1 gf·cm.

As shown in FIG. 15, the sensory evaluation result in Example A-7 was between "somewhat difficult to hold" and "difficult to hold", and somewhat close to "difficult to hold". Accordingly, ease of holding of the flavor aspirator 11 was evaluated as poorer than "moderate".

Comparative Example B-1

In Comparative Example B-1, the weight of the second weight-concentrated part 32 accounts for 83% of the total weight of the flavor aspirator 11. In Comparative Example B-1, the position of the center of gravity is set so that the value of (the length from the mouthpiece end 13A to the center of gravity)/(the total length) is 0.17.

In Comparative Example B-1, the moment when the point where the value of (the length from the mouthpiece end 13A to the point)/(the total length) is 0.3 is gripped is −20.2 gf·cm.

As shown in FIG. 15, the sensory evaluation result of Comparative Example B-1 was between "somewhat difficult to hold" and "difficult to hold", and somewhat close to "difficult to hold". Accordingly, ease of holding of the flavor aspirator 11 was evaluated as poorer than "moderate".

Example B-2

In Example B-2, the weight of the second weight-concentrated part 32 accounts for 85% of the total weight of the flavor aspirator 11. In Example B-2, the position of the center of gravity is set in such a manner that the value of (the length from the mouthpiece end 13A to the center of gravity)/(the total length) is 0.21.

In Example B-2, the moment when the point where the value of (the length from the mouthpiece end 13A to the point)/(the total length) is 0.3 is gripped is 10.1 gf·cm.

As shown in FIG. 15, the sensory evaluation result of Example B-2 was between "moderate" and "somewhat difficult to hold", and close to "moderate". Accordingly, ease of holding of the flavor aspirator 11 was evaluated as close to "moderate".

Example B-3

In Example B-3, the weight of the second weight-concentrated part 32 accounts for 82% of the total weight of the flavor aspirator 11. In Example B-3, the position of the center of gravity is set in such a manner that the value of (the length from the mouthpiece end 13A to the center of gravity)/(the total length) is 0.25.

In Example B-3, the moment when the point where the value of (the length from the mouthpiece end 13A to the point)/(the total length) is 0.3 is gripped is −6.2 gf·cm.

As shown in FIG. 15, the result of the sensory evaluation result in Example B-3 was "moderate". Accordingly, ease of holding of the flavor aspirator 11 was evaluated as "moderate".

Example B-4

In Example B-4, the weight of the second weight-concentrated part 32 accounts for 86% of the total weight of the flavor aspirator 11. In Example B-4, the position of the center of gravity is set in such a manner that the value of (the length from the mouthpiece end 13A to the center of gravity)/(the total length) is 0.30.

In Example B-4, the moment when the point where the value of (the length from the mouthpiece end 13A to the point)/(the total length) is 0.3 is gripped is −0.7 gf·cm.

As shown in FIG. 15, the sensory evaluation result in Example B-4 was between "moderate" and "somewhat easy to hold", and close to "somewhat close to hold". Accordingly, ease of holding of the flavor aspirator 11 was evaluated as "somewhat easy to hold".

Example B-5

In Example B-5, the weight of the second weight-concentrated part 32 accounts for 80% of the total weight of the flavor aspirator 11. In Example B-5, the position of the center of gravity is set in such a manner that the value of (the length from the mouthpiece end 13A to the center of gravity)/(the total length) is 0.35.

In Example B-5, the moment when the point where the value of (the length from the mouthpiece end 13A to the point)/(the total length) is 0.3 is gripped is 5.2 gf·cm.

As shown in FIG. 15, a result of the sensory evaluation result in Example B-5 was about halfway between "easy to hold" and "somewhat easy to hold". Accordingly, ease of holding of the flavor aspirator 11 was evaluated as "easy to hold".

Example B-6

In Example B-6, the weight of the second weight-concentrated part 32 accounts for 50% of the total weight of the flavor aspirator 11. In Example B-6, the position of the center of gravity is set in such a manner that the value of (the length from the mouthpiece end 13A to the center of gravity)/(the total length) is 0.41.

In Example B-6, the moment when the point where the value of (the length from the mouthpiece end 13A to the point)/(the total length) is 0.3 is gripped is 11.6 gf·cm.

As shown in FIG. 15, a result of the sensory evaluation result of Example B-6 was about halfway between "somewhat easy to hold" and "moderate". Accordingly, ease of holding of the flavor aspirator 11 was evaluated as better than "moderate".

Example B-7

In Example B-7, the weight of the second weight-concentrated part 32 accounts for 50% of the total weight of the flavor aspirator 11. In Example B-7, the position of the center of gravity is set in such a manner that the value of (the length from the mouthpiece end 13A to the center of gravity)/(the total length) is 0.40.

In Example B-7, the moment when the point where the value of (length from the mouthpiece end 13A to the point)/(total length) is 0.3 is gripped is 15.5 gf·cm.

As shown in FIG. 15, the sensory evaluation result of Example B-7 was between "moderate" and "somewhat difficult to hold", and somewhat close to "somewhat difficult to hold". Accordingly, ease of holding of the flavor aspirator 11 was evaluated as poorer than "moderate".

Comparative Example B-8

In Comparative Example B-8, the weight of the second weight-concentrated part 32 constitutes 53% of the total weight of the flavor aspirator 11. In Comparative Example B-8, the position of the center of gravity is set so that the value of (length from the mouthpiece end 13A to the center of gravity)/(total length) is 0.50.

In Comparative Example B-8, the moment when the point where the value of (the length from the mouthpiece end 13A to the point)/(the total length) is 0.3 is gripped is 31.0 gf·cm.

As shown in FIG. 15, the sensory evaluation result in Comparative Example B-8 was between "somewhat difficult to hold" and "difficult to hold", and close to "difficult to hold". Accordingly, ease of holding of the flavor aspirator 11 was evaluated as "difficult to hold".

As shown in FIG. 16 and FIG. 17, the results of the foregoing examples were analyzed. The graph of FIG. 16 shows the relationships between the moments in Example A-1 to Example A-6, Comparative Example A-7, Comparative Example B-1, Example B-2 to Example B-7, Comparative Example B-8, and the results of the sensory evaluation of these examples. These moments were calculated by the method described in the first embodiment. The graph of FIG. 17 shows the relationship between the absolute values of the moments in Example A-1 to Example A-6, Comparative Example A-7, Comparative Example B-1, Example B-2 to Example B-7, Comparative Example B-8, and the results of the sensory evaluation of these examples. FIG. 17 further shows a regression equation (linear regression equation) calculated from the absolute values of the moments in Example A-1 to Example A-6, Comparative Example A-7, Comparative Example B-1, Example B-2 to Example B-7 and Comparative Example B-8, and the results of the sensory evaluation of these examples. The regression equation obtained by the regression analysis is as follows:

$$y = -0.1006x + 3.1319 \quad \text{Expression (1)}$$

Thus, it can be seen that the absolute values of the moments and the results of the sensory evaluation show a negative correlation. In addition, the coefficient of determination $R^2$ of this regression line is as follows:

$$R^2 = 0.7491 \geq 0.5,$$

and it can be said that the accuracy of linear regression is good. From the equation (1), x when y=2.0 (moderate) is x=11.2514 ... ≈11.25.

Therefore, when x is 11.25 or less, the result of the sensory evaluation becomes "moderate" or better. Therefore, in order to realize the "easy to hold" flavor aspirator 11, it is desirable to set at least an absolute value for the moment when the point where the value of (the length from the mouthpiece end 13A to the point)/(the total length) is 0.3 is gripped to 11.25 or less.

In the flavor aspirator 11 of each of Examples A-2 to A-4 and B-3 to B-5, the absolute values of the moment when a point where the value of (the length from the mouthpiece end 13A to the point)/(the total length) is 0.3 is gripped is 11.25 gf·cm or less. According to this design, it is possible to realize a so-called "easy-to-hold" flavor aspirator 11 by reducing load applied to the user's fingers when being gripped.

The applicant has also recognized the following matters as inventions.

[1]

A flavor aspirator comprising:

a weight-concentrated part, wherein the weight-concentrated part has a value of (a length from the mouthpiece end to the part)/(a total length defined by the length of from the mouthpiece end to the distal end), which is in a range of 0.15 to 0.45 and accounts for 45% or more of the total weight, or a value of (the length from the mouthpiece end to the part)/(the total length) is in a range of 0 to 0.2 and in a range of 0.9 to 1.0, and accounts for 45% or more of the total weight, and a value of (a length from the mouthpiece end to the center of gravity)/(the total length) is in a range of 0.20 to 0.45.

[2]

The flavor aspirator described in [1], wherein a value of (the length from the mouthpiece end to the center of gravity)/(the total length) is in a range of 0.22 to 0.44.

[3]

The flavor aspirator described in [1], wherein a value of (the length from the mouthpiece end to the center of gravity)/(the total length) is in a range of 0.21 to 0.41.

REFERENCE SIGNS LIST

11 ... Flavor aspirator, 13 ... Mouthpiece, 14 ... Distal end, 15 ... Battery, 16 ... Aerosol source, 25 ... First weight-concentrated part, 26 ... Midpoint position, 28 ... Member, 32 ... Second weight-concentrated part, 32A ... Part in the vicinity of the mouthpiece end, 32B ... Part in the vicinity of the distal end, 41 ... Divided segment, 42 ... Other divided segment

The invention claimed is:

1. A flavor aspirator comprising:
a housing including a mouthpiece end and a distal end, the housing extending from the mouthpiece end to the distal end; and
a weight-concentrated part including a first part provided in a vicinity of the mouthpiece end and a second part provided in a vicinity of the distal end, and that has a weight accounting for at least approximately half of the total weight, the weight being a sum of a weight of the first part and a weight of the second part,
wherein a value of (a length from the mouthpiece end to the center of gravity)/(a total length defined by a length from the mouthpiece end to the distal end) is in a range of 0.20 to 0.45, and
wherein the flavor aspirator has a rod shape or a cylindrical shape.

2. The flavor aspirator according to claim 1, wherein the weight-concentrated part has a weight accounting for 45% or more of a total weight,
wherein the weight is a sum of a weight of a part where a value of (a length from the mouthpiece end to the weight-concentrated part)/(the total length) falls within a range of 0 to 0.2 and a weight of a part where a value of (a length from the mouthpiece end to the weight-concentrated part)/(the total length) falls within a range of 0.9 to 1.0 and accounts for 45% of the total weight.

3. The flavor aspirator according to claim 1, wherein an absolute value of a moment when a point where a value of (a length from the mouthpiece end to the weight-concentrated part)/(the total length) of 0.3 is gripped is 15.5 gf·cm or less.

4. The flavor aspirator according to claim 3, wherein an absolute value of a moment when a point where a value of (a length from the mouthpiece end to the weight-concentrated part)/(the total length) of 0.3 is gripped is 14.5 gf·cm or less.

5. The flavor aspirator according to claim 3, wherein a value of (a length from the mouthpiece end to the center of gravity)/(the total length) is in a range of 0.25 to 0.44.

6. The flavor aspirator according to claim 5, wherein a value of (a length from the mouthpiece end to the center of gravity)/(the total length) is in a range of 0.3 to 0.44.

7. The flavor aspirator according to claim 1, wherein an absolute value of a moment when a point where a value of (a length from the mouthpiece end to the weight-concentrated part)/(a total length defined by a length from the mouthpiece end to the distal end) is 0.3 is gripped is 11.25 gf·cm or less.

8. The flavor aspirator according to claim 1, wherein the total weight is in a range of 10.4 g to 15.5 g or less.

9. The flavor aspirator according to claim 1, wherein the weight-concentrated part is at least partially made of a metal.

10. The flavor aspirator according to claim 1, wherein the weight-concentrated part has a weight-adjustment member.

11. The flavor aspirator according to claim 1, wherein when the flavor aspirator is divided by a plane including a central axis extending from the mouthpiece end to the distal end, one of the divided segments is 1.5 times larger than the other of the divided segments.

12. A flavor aspirator, comprising:
a housing including a mouthpiece end and a distal end, the housing extending from the mouthpiece end to the distal end; and
a weight-concentrated part including a first part provided in a vicinity of the mouthpiece end and a second part provided in a vicinity of the distal end,
wherein the weight-concentrated part has a weight accounting for at least approximately half of a total weight,
wherein the weight of the weight-concentrated part being a sum of a weight of the first part and a weight of the second part,
wherein the weight of the first part is heavier than the weight of the second part, and
wherein the flavor aspirator has a rod shape or a columnar shape.

13. The flavor aspirator according to claim 1, wherein the flavor aspirator is non-combustion type.

14. The flavor aspirator according to claim 1, comprising:
an aerosol source;
a heat source that generates aerosol by heating a liquid supplied from the aerosol source; and
a power supply for supplying electric power to the heat source.

15. The flavor aspirator according to claim 1, further comprising:
a battery housed in the housing,
wherein the battery constitutes a part of the second part of the weight-concentrated part.

16. The flavor aspirator according to claim 12, further comprising:
a battery housed in the housing,
wherein the battery constitutes a part of the second part of the weight-concentrated part.

17. The flavor aspirator according to claim 1, wherein the housing is made of resin.

18. The flavor aspirator according to claim 12, wherein the housing is made of resin.

* * * * *